(12) United States Patent
Wawro et al.

(10) Patent No.: US 8,535,233 B2
(45) Date of Patent: Sep. 17, 2013

(54) BLOOD PRESSURE MEASURING APPARATUS

(75) Inventors: Thaddeus J. Wawro, Auburn, NY (US); Raymond A. Lia, Auburn, NY (US)

(73) Assignee: Welch Allyn, Inc., Skaneateles Falls, NY (US)

(*) Notice: Subject to any disclaimer, the term of this patent is extended or adjusted under 35 U.S.C. 154(b) by 687 days.

(21) Appl. No.: 11/513,608

(22) Filed: Aug. 31, 2006

(65) Prior Publication Data

US 2006/0293600 A1 Dec. 28, 2006

Related U.S. Application Data

(63) Continuation-in-part of application No. 11/230,117, filed on Sep. 19, 2005, now Pat. No. 7,780,603, which is a continuation-in-part of application No. 10/456,704, filed on Jun. 5, 2003, now Pat. No. 7,722,542, which is a continuation-in-part of application No. 09/929,501, filed on Aug. 14, 2001, now Pat. No. 6,615,666, which is a continuation-in-part of application No. 09/669,474, filed on Sep. 25, 2000, now Pat. No. 6,422,086.

(51) Int. Cl.
*A61B 5/02* (2006.01)

(52) U.S. Cl.
USPC .......................................... 600/499; 600/490

(58) Field of Classification Search
USPC ....................... 600/485–499; 606/201–203
See application file for complete search history.

(56) References Cited

U.S. PATENT DOCUMENTS

| | | | |
|---|---|---|---|
| 1,106,341 A | 8/1914 | Bristol |
| 1,328,876 A | 1/1920 | Hill |
| 1,377,032 A | 5/1921 | Starling et al. |
| 2,087,494 A | 7/1937 | Annin |
| 2,341,137 A | 2/1944 | Damron |
| 2,564,669 A | 8/1951 | Brady |
| 2,636,394 A | 4/1953 | Melchior |
| 2,678,040 A | 5/1954 | Poole et al. |
| 2,714,379 A | 8/1955 | Raines |
| 3,279,459 A | 10/1966 | Schenker |
| 3,606,880 A | 9/1971 | Ogle, Jr. |
| 3,633,567 A | 1/1972 | Sarnoff |
| 3,635,214 A | 1/1972 | Rand et al. |
| 3,659,592 A | 5/1972 | Natkanski |
| 3,756,239 A | 9/1973 | Smythe |
| 3,757,772 A | 9/1973 | Goldblat et al. |

(Continued)

FOREIGN PATENT DOCUMENTS

| | | |
|---|---|---|
| CA | 2100854 | 1/1994 |
| DE | 0591564 | 1/1934 |

(Continued)

OTHER PUBLICATIONS

International Search Report Corresponding to PCT/US2007/016828; Mailed Jan. 18, 2008 (9 pages).

(Continued)

*Primary Examiner* — Patricia Mallari
*Assistant Examiner* — Tiffany Weston

(57) ABSTRACT

Adaptive attachments used in combination with a blood pressure cuff enable various blood pressure measurements to be taken in a hospital or other setting having various single and/or dual lumen manual or electronic blood pressure measuring equipment with a single, patient-worn cuff.

44 Claims, 24 Drawing Sheets

(56) References Cited

U.S. PATENT DOCUMENTS

| | | |
|---|---|---|
| 3,760,795 A | 9/1973 | Adelhed |
| 3,773,036 A | 11/1973 | Weyer |
| 3,797,315 A | 3/1974 | Halpern |
| 3,805,618 A | 4/1974 | Csaposs et al. |
| 3,874,242 A | 4/1975 | Csaposs et al. |
| 3,906,937 A | 9/1975 | Aronson |
| D244,879 S | 6/1977 | Manno |
| 4,036,061 A | 7/1977 | Speidel |
| 4,036,216 A * | 7/1977 | Ramsey, III ................. 600/488 |
| 4,040,298 A | 8/1977 | Lee et al. |
| 4,248,241 A | 2/1981 | Tacchi |
| 4,255,970 A | 3/1981 | Van Pottelberg |
| D269,905 S | 7/1983 | Tamm |
| 4,501,271 A | 2/1985 | Clifton et al. |
| 4,535,938 A | 8/1985 | Lindabury, Sr. |
| 4,543,824 A | 10/1985 | Marterer |
| 4,549,550 A | 10/1985 | Kami |
| 4,605,010 A | 8/1986 | McEwen |
| 4,653,506 A | 3/1987 | Romanovskaya |
| 4,685,336 A | 8/1987 | Lee |
| 4,726,382 A | 2/1988 | Boehmer et al. |
| 4,726,686 A | 2/1988 | Wolf et al. |
| 4,802,370 A | 2/1989 | EerNisse et al. |
| 4,844,512 A | 7/1989 | Gahwiler |
| 4,896,676 A | 1/1990 | Sasaki |
| 4,920,971 A | 5/1990 | Blessinger |
| 4,967,758 A | 11/1990 | Masciarotte |
| 4,979,953 A | 12/1990 | Spence |
| 5,003,981 A | 4/1991 | Kankkunen et al. |
| 5,025,792 A | 6/1991 | Hon et al. |
| 5,048,533 A | 9/1991 | Muz |
| 5,101,830 A | 4/1992 | Duffy et al. |
| 5,137,024 A * | 8/1992 | Souma ................. 600/498 |
| 5,179,957 A | 1/1993 | Williams |
| 5,181,422 A | 1/1993 | Leonard et al. |
| 5,220,925 A | 6/1993 | Hishida |
| 5,228,448 A | 7/1993 | Byrd |
| 5,275,444 A | 1/1994 | Wythoff |
| 5,320,169 A | 6/1994 | Delatorre |
| 5,392,782 A | 2/1995 | Garrett |
| D356,155 S | 3/1995 | Caven |
| 5,396,894 A * | 3/1995 | Eide et al. ................. 600/499 |
| 5,400,787 A | 3/1995 | Marandos |
| 5,413,582 A * | 5/1995 | Eaton ................. 606/202 |
| 5,424,598 A | 6/1995 | Corbett |
| 5,511,552 A * | 4/1996 | Johnson ................. 600/499 |
| 5,513,534 A | 5/1996 | Brechbuhl et al. |
| 5,513,643 A | 5/1996 | Suite |
| 5,626,142 A | 5/1997 | Marks |
| 5,660,182 A * | 8/1997 | Kuroshaki et al. ................. 600/499 |
| 5,678,558 A | 10/1997 | Johnson |
| 5,690,672 A | 11/1997 | Cohen |
| 5,746,213 A | 5/1998 | Marks |
| 5,753,821 A | 5/1998 | Chou |
| 5,819,739 A | 10/1998 | Levavi et al. |
| 5,882,515 A | 3/1999 | Lacy et al. |
| 5,904,655 A | 5/1999 | Brackett |
| 5,966,829 A | 10/1999 | Lia et al. |
| 6,036,718 A | 3/2000 | Ledford et al. |
| 6,082,170 A | 7/2000 | Lia et al. |
| 6,095,983 A * | 8/2000 | Wawro ................. 600/485 |
| 6,120,458 A | 9/2000 | Lia et al. |
| 6,152,880 A | 11/2000 | Okada |
| 6,168,566 B1 | 1/2001 | Lia et al. |
| 6,189,558 B1 | 2/2001 | Traylor |
| 6,213,953 B1 | 4/2001 | Reeves |
| 6,234,972 B1 | 5/2001 | Lia et al. |
| 6,245,023 B1 | 6/2001 | Clemmons |
| 6,245,024 B1 | 6/2001 | Montagnino et al. |
| 6,344,025 B1 * | 2/2002 | Inagaki et al. ................. 600/490 |
| 6,346,084 B1 * | 2/2002 | Schnell et al. ................. 600/561 |
| 6,394,977 B1 | 5/2002 | Taylor et al. |
| 6,422,086 B1 | 7/2002 | Dromms et al. |
| 6,475,153 B1 | 11/2002 | Khair et al. |
| 6,481,291 B1 | 11/2002 | Lia et al. |
| 6,506,162 B1 | 1/2003 | Tseng |
| 6,525,238 B2 | 2/2003 | Corrales |
| 6,551,249 B2 | 4/2003 | Ashida et al. |
| 6,578,428 B1 | 6/2003 | Dromms et al. |
| 6,615,666 B1 | 9/2003 | Lia et al. |
| 6,616,666 B1 | 9/2003 | Michelson |
| 6,682,547 B2 | 1/2004 | McEwen et al. |
| 6,746,406 B2 | 6/2004 | Lia et al. |
| 6,796,186 B2 | 9/2004 | Lia et al. |
| D532,519 S | 11/2006 | Aujla et al. |
| 7,722,542 B2 | 5/2010 | Lia et al. |
| 2001/0005777 A1 * | 6/2001 | Nakagawa et al. ........... 600/499 |
| 2002/0099297 A1 | 7/2002 | Nakagawa et al. |
| 2002/0156382 A1 | 10/2002 | Freund et al. |
| 2003/0036690 A1 | 2/2003 | Geddes et al. |
| 2004/0083816 A1 | 5/2004 | Lia et al. |
| 2004/0092831 A1 | 5/2004 | Hood, Jr. |
| 2004/0181156 A1 * | 9/2004 | Kingsford et al. ............ 600/490 |
| 2006/0089668 A1 | 4/2006 | Warburton |
| 2006/0217618 A1 | 9/2006 | Lia et al. |
| 2007/0135836 A1 | 6/2007 | McEwen et al. |
| 2007/0244506 A1 | 10/2007 | McEwen et al. |

FOREIGN PATENT DOCUMENTS

| | | |
|---|---|---|
| EP | 0591 564 A1 | 4/1994 |
| EP | 0 705 563 A1 | 4/1996 |
| EP | 1945096 | 7/2008 |
| EP | 1992281 | 11/2008 |
| FR | 2592297 A | 7/1987 |
| GB | 740181 | 11/1955 |
| WO | 00/22983 A | 4/2000 |
| WO | 00/40941 | 7/2000 |
| WO | WO 02/26128 | 4/2002 |
| WO | WO 2007/035271 | 3/2007 |

OTHER PUBLICATIONS

International Search Report dated Feb. 5, 2007 from corresponding PCT/US/06/34909(2 pgs).

Operating Instruction Manual, "Welch Allyn® DuraShock™ Integrated Aneroid Sphygmomanometer", pp. 1-7, 2001.

European Search Report for EP Application No. 06790195.9; mailed Oct. 30, 2009; 11 pages.

"Plastics Plus, Inc. Biodegradable Solution PPI BD-0701"; Published Oct. 2008 (8 pages).

International Search Report for PCT/US06/34909, Dated Feb. 5, 2007 (6 pages).

"Socket", The American Heritage Dictionary of the English Language .COPYRGT. Houghton Mifflin Company 2003. Retrieved Nov. 7, 2007—http://www.credoreference.com/entry/4133272.

* cited by examiner

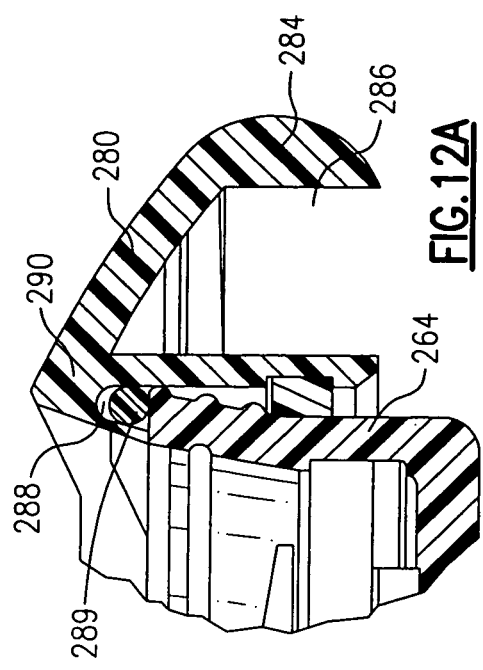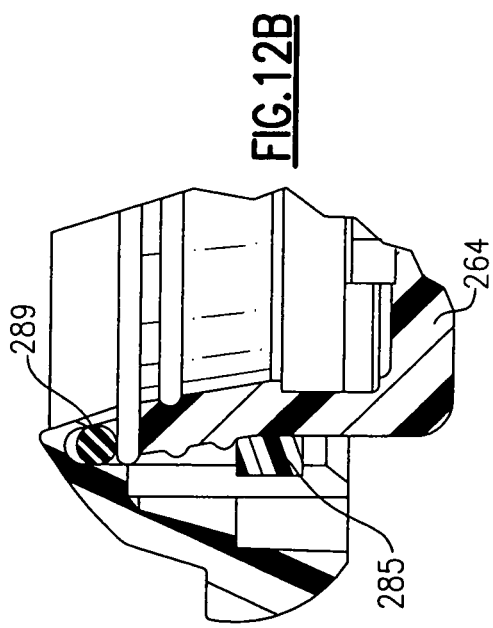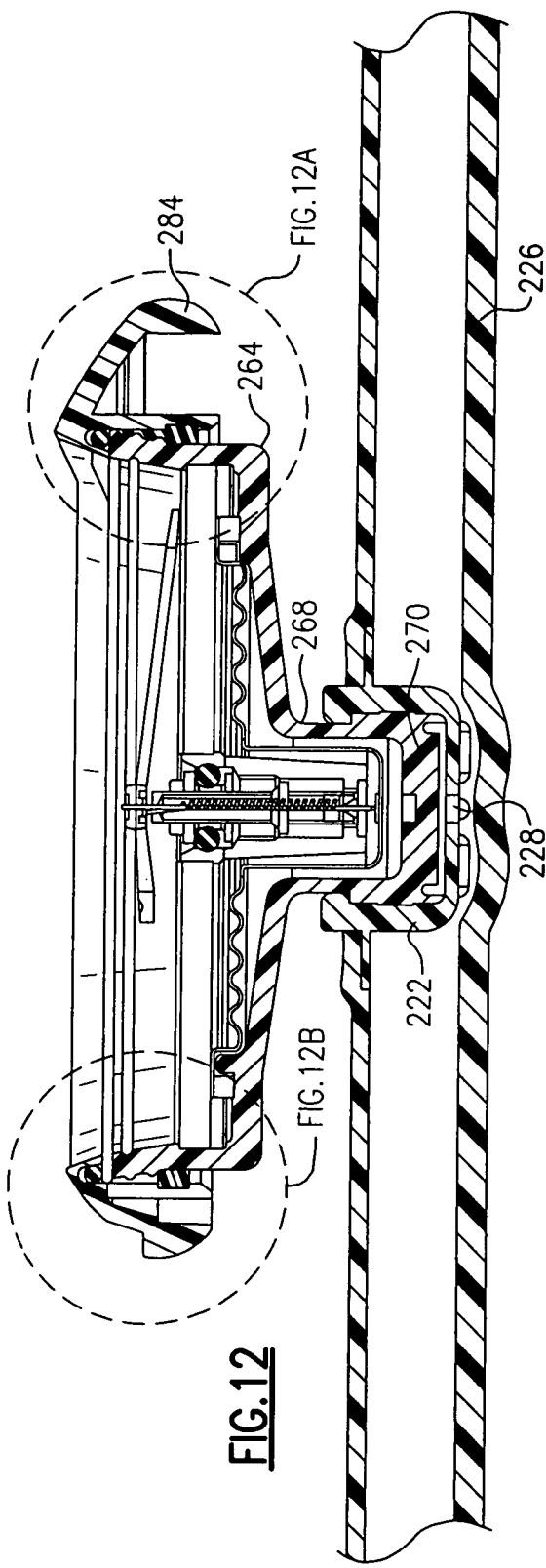

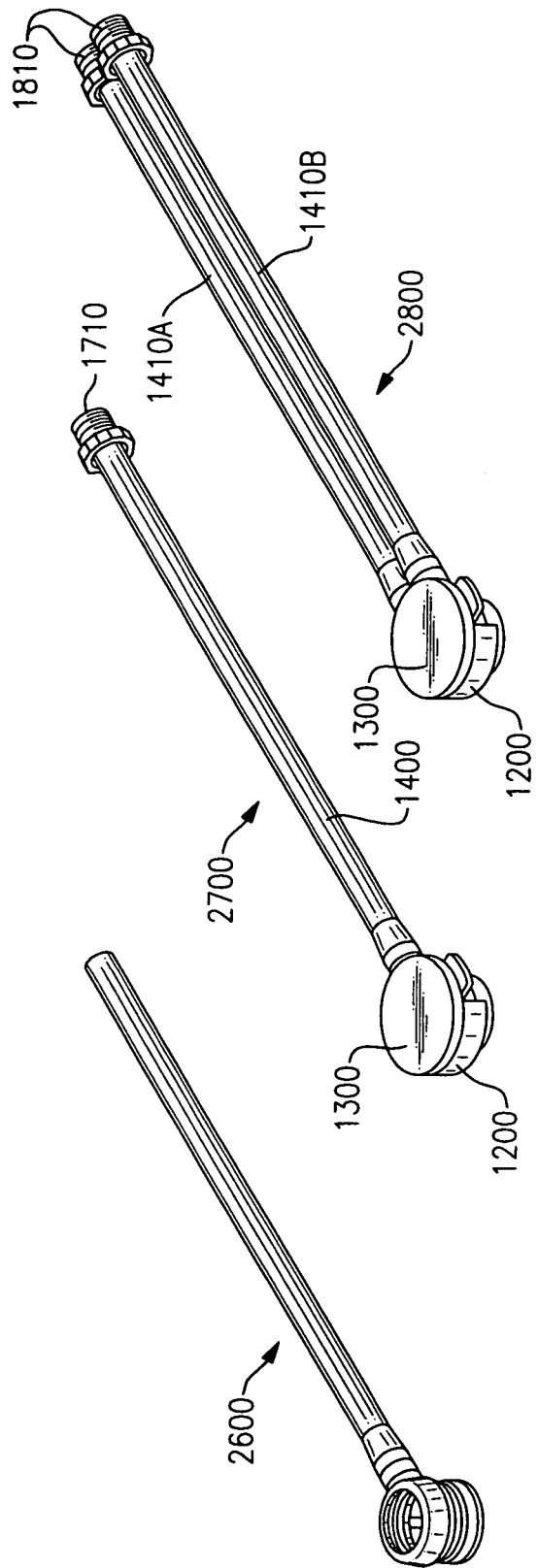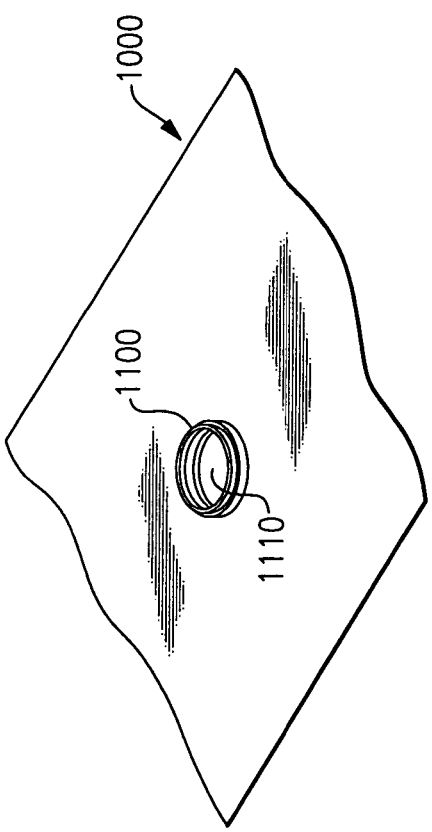
FIG. 29

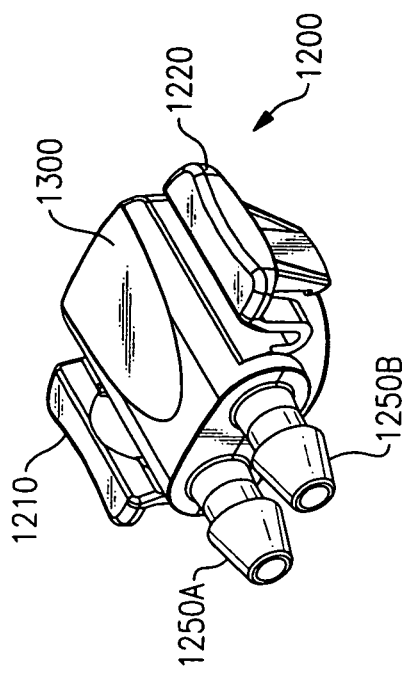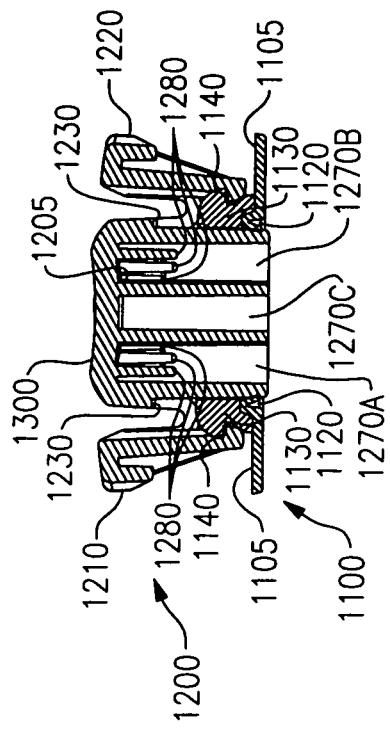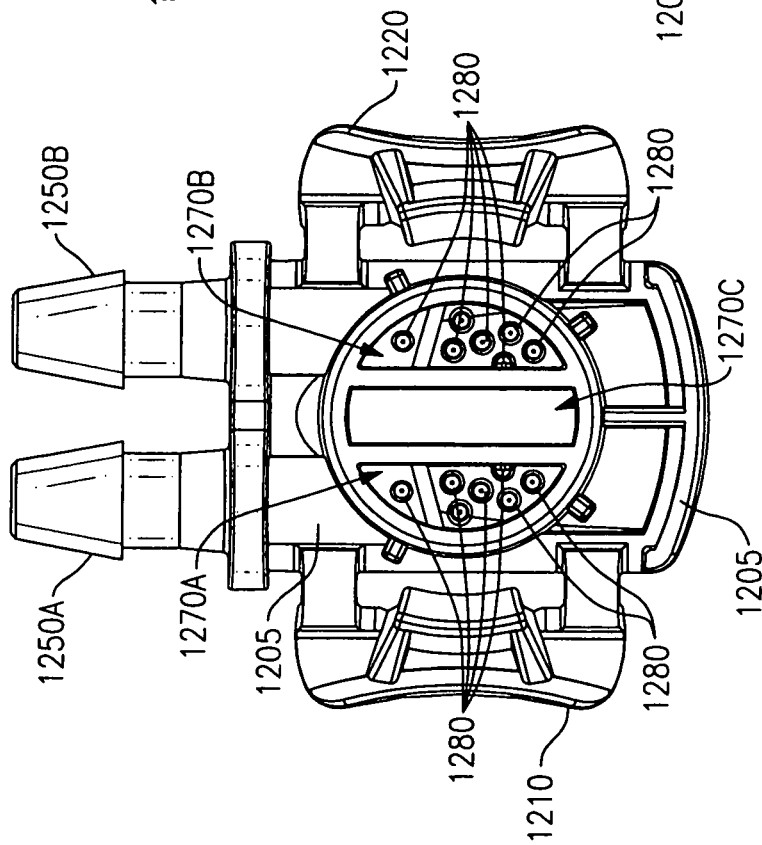

BLOOD PRESSURE MEASURING APPARATUS

CROSS REFERENCE TO RELATED APPLICATIONS

This application claims priority as a continuation in part (CIP) application to copending and commonly owned U.S. patent application Ser. No. 11/230,117, entitled BLOOD PRESSURE MEASURING APPARATUS, which was filed on Sep. 19, 2005 and claimed priority as a CIP application to U.S. patent application Ser. No. 10/456,704, which was filed on Jun. 5, 2003 and claimed priority as a CIP application to U.S. patent application Ser. No. 09/929,501, which was filed on Aug. 14, 2001, issued as U.S. Pat. No. 6,615,666 on Sep. 9, 2003, and claimed priority as a CIP application to U.S. patent application Ser. No. 09/669,474, which was filed on Sep. 25, 2000, and issued as U.S. Pat. No. 6,422,086 on Jul. 23, 2002, wherein each of the Ser. Nos. 11/230,117, 10/456,704, 09/929,501 and 09/669,474 applications is incorporated by reference herein in its entirety.

FIELD OF THE INVENTION

The invention relates to the field of measuring instruments, and more particularly to a technique and related apparatus for enabling a plurality of blood pressure measurements to be interchangeably performed with various discrete systems, such as within a hospital environment.

BACKGROUND OF THE INVENTION

Pressure measuring devices such as sphygmomanometers, that are used to measure the arterial blood pressure of a patent, typically include a pneumatic bulb which inflates a pressure chamber of an attached sleeve that is fitted over a limb (i.e., an arm or a leg) of the patient. A diaphragm or bellows assembly, responsive to changes in fluid pressure of the pneumatic bulb and the sleeve pressure chamber, is positioned in a gage housing which is fluidly connected to the pressure chamber of the sleeve through flexible tubes or hoses. In a mechanical gage housing, a pointer of a dial indicator is interconnected to the bellows assembly through a movement mechanism that is retained within the gage housing, whereby inflation of the bellows causes corresponding circumferential movement of the pointer, enabling a blood pressure measurement procedure to be carried out by a caregiver.

Typically, the above referred to movement mechanisms are quite intricate and complex, and are akin in terms of their manufacture and precision to Swiss watches. For example, and in one such movement mechanism, a pair of diaphragm springs are attached adjacent opposing ends of a spindle. A bottom end of the spindle is placed in contact with the bellows assembly and a twisted bronze band perpendicularly disposed at the top end of the spindle is connected in parallel by a horizontally disposed spring bent part. As the spindle deflects axially in response to the inflation of the bellows, the bent spring part is also caused to deflect, thereby causing the band to twist. The pointer, attached to the bronze band, therefore is caused to rotate in relation to an adjacent dial face.

Devices, such as the foregoing, include numerous moving and relatively complex components, some or each of having numerous bearing surfaces. Therefore, such known devices must be manufactured with relatively strict tolerance margins and significant associated costs in terms of both precision and failure rate in order to minimize errors.

In addition, any adjustments required after assembly of the above mechanisms, such as to null the pointer or adjust the sensitivity of the device, require substantial tear down or at least some undesired disassembly.

Furthermore, discrete and separate elements are typically required within the instrument housing for independently supporting the movement mechanism and the bellows assembly, respectively, and for defining an expansion chamber for the bellows assembly there between.

A more recent and simplified movement mechanism is described in U.S. Pat. No. 5,996,829, incorporated by reference in its entirety. This mechanism includes a vertically disposed axial cartridge having a spirally wrapped ribbon spring with one end mounted to an axially movable elongate shaft and the remaining end of the spring being attached to a fixed tubular sleeve. A bottom portion of the elongate shaft is positioned relative to an expandable diaphragm or bellows, wherein subsequent axial translation of the shaft, caused by movement of the diaphragm, elongates the spirally wound ribbon spring and produces repeatable circumferential movement of a pointer supported at the top end of the shaft. The above movement mechanism is far smaller and more lightweight than those previously known due to its simplified construction.

A further advance, described in U.S. Pat. No. 6,168,566, also incorporated by reference in its entirety, permits the design of a housing retaining the movement mechanism described in the '829 patent to be even more compact.

One feature common to the above pressure measuring devices is the need to fluidly interconnect the gage housing containing the movement mechanism, the dial face and the indicating member with the interior of the inflatable sleeve. This interconnection is typically done using an elongated hose that is connected to a barb or coupling located on the sleeve exterior at one end of the hose and to an inlet port disposed on one end of the gage housing. It is a general object in the field to simplify the manufacture of these devices and to better integrate the design thereof.

More recently, electronic versions of pressure measuring devices have become much more prevalent and conspicuous in their use in the field. These devices such as those manufactured by Omron, Inc. among others can be mounted to the arm or wrist of a patient. These devices have a battery powered electronically based device that converts the output from the sleeve into a pressure reading output to the user. There is still reliance, however, upon inflation and deflation of an inflatable sleeve and more particularly, there is a fluid interconnection between the interior of the sleeve and the interior of the gage housing. In addition and to date, all of these devices have always been part of an integrated assembly, including the sleeve, whereby replacement has required replacement of not only the sleeve, but also the tethered electronic components.

With the emergence of such electronic equipment, there are now numerous effective ways to measure blood pressure through use of a variety of different types of both manual and electronic blood pressure measurement equipment and devices. There are two general types of manual or mechanical blood pressure measurement equipment that remain in circulation and that continue to be manufactured and used indiscriminately today. A first type of measurement device is in communication with a cuff/sleeve through a single lumen hose attachment that is utilized to inflate and deflate pressure in the cuff. A second type of blood pressure measurement device is in communication with a cuff/sleeve through a dual lumen hose attachment in which one lumen is again utilized to inflate and deflate pressure in the cuff and the second lumen allows for monitoring of the pressure within the cuff. Similarly, there are also different types of electronic blood pressure measurement devices, some of which rely upon hose attachments having one lumen, and others that utilize a dual lumen hose attachment. Moreover, some manufacturers have designed manual and electronic blood pressure measurement equipment that is connected to a hose attachment by one type of connector (e.g., a screw/luer type), whereas other manufacturers may require such connection be made to their equipment via a different type of connector (e.g., a luer lock or bayonet type).

Currently, there is no standard that dictates how manual or electronic blood pressure measurement devices must be designed. Moreover, hospitals and HMO treatment centers have varying needs and are budget conscious to an extent whereby most have not withdrawn older, still functioning blood pressure measurement devices from use despite also having begun to utilize newer, more sophisticated equipment. These circumstances have led to a situation in which many hospitals and HMO treatment centers have several different types (e.g., manual, electronic, reliant upon a single lumen hose attachment, reliant upon a dual lumen hose attachment, utilizing different connectors, etc.) of blood pressure measurement equipment for use at various stations on their premises.

The preceding situation, in turn, has created a problem in which vital time and manpower is being lost while switching between and among these different types of blood pressure measurement equipment. Although this problem can exist in any medical setting, it is most salient within a hospital environment, where it is often important to continually monitor the blood pressure of a patient, since a sudden change in the patient's blood pressure could be indicative of an improvement or set back in the patient's condition, or could aid in the overall diagnostic and/or treatment thereof.

At present, such continuous monitoring is generally commenced by wrapping a first cuff/sleeve (having at least one pre-attached single lumen or dual lumen hose) onto a patient in order to take the patient's blood pressure through use of a first blood pressure measurement device, either within an ambulance during transport to a hospital or upon arrival at the initial assessment/treatment area (e.g., triage unit, diagnosis station) of a hospital. It is generally necessary to remove the initial cuff/sleeve and attached hose combination prior to transporting the patient to his or her next destination within the hospital, e.g., a trauma room or an imaging room, at which a new sleeve (again with at least one single lumen or dual lumen pre-attached hose) of the proper size must be located and attached to enable blood pressure monitoring to continue through use of a different blood pressure measurement device. For example, the first blood pressure measurement device may be a manual or electronic device and the second an incompatible (e.g., due to the number of lumens in the pre-attached hose, the connector required, etc.) manual or electronic blood pressure device.

Under typical circumstances, such detaching, locating and reattaching steps might be performed several times while the patient is being initially evaluated and/or after the patient is admitted to the hospital. This is because, as noted above, many hospitals routinely utilize both manual and electronic blood pressure measurement equipment, some or all of which may be incompatible the with the currently worn cuff/sleeve with at least one hose attachment (e.g., due to being manual versus electronic, the type of connector required, the number of lumens within the attached hose, etc.). Even in a best-case scenario, each round of detaching, locating and reattaching steps are inconvenient because they command the attention, however brief, of medical personnel who could otherwise be performing different tasks. And at worst, the seconds to minutes that can be spent in locating, attaching, detaching and reattaching each new cuff/sleeve with a pre-attached hose could have life-impacting consequences for a patient.

Moreover, due to the chaos that often can be encountered when evaluating a patient in a hospital, especially in an emergency department setting, it is not uncommon for the at least one pre-attached hose that is connected to the cuff/sleeve to become kinked to an extent that would prevent further blood measurements from being taken with sufficient accuracy. Because the hose is pre-attached to the sleeve, once kinking occurs it might becomes necessary to remove the sleeve with pre-attached hose and then to locate and attach an entirely new sleeve with its own pre-attached hose. This is problematic for the same reasons noted above, plus it can introduce even more chaos into the emergency department environment.

Thus, there is a need for a procedure to reliably measure blood pressure and that also will better enable a wide range of electronic or manual blood pressure measurements to be taken interchangeably and with minimal disruptions through use of a wide range of manual or electronic blood pressure measurement equipment and devices, such as those found in a hospital or HMO treatment center environment.

SUMMARY OF THE INVENTION

These and other needs are met by the present invention, which provides systems, methods and kits for interchangeably enabling blood pressure measurements to be performed on a patient through use of various different blood pressure measurement equipment or devices while enabling the same cuff/sleeve to be worn by the patient the entire time, if desired. In other words, through use or implementation of the systems, methods and kits of the present invention, a patient can wear the same cuff/sleeve while numerous blood pressure measurements are performed using a wide variety of manual or electronic blood pressure measurement equipment, regardless of the design or manufacturer of the various equipment, thus obviating the need to repeatedly detach a cuff/sleeve and then locate and reattach a new sleeve/cuff. Additionally, the systems, methods and kits of the present invention enable any of several pieces of blood pressure measurement equipment to be individually connected to any of multiple patients regardless of the size and type of cuff each patient is wearing and/or irrespective of the design and manufacturer of the pieces of blood pressure measurement equipment.

According to an exemplary aspect of the present invention, an inflatable cuff is adapted to be wrapped about a limb of a patient, wherein the cuff includes an interior chamber and an exterior surface. The cuff can be disposable (i.e., meant for use only on that patient) or durable (i.e., reusable on more than one patient). A first adapter is connected to the cuff, the first adapter including an opening that provides direct fluid communication between the exterior surface and the interior chamber of the cuff. A second adapter also can be provided and, when so, is releasably connected to and in direct fluid communication with the first adapter, wherein the second adapter allows individual interchangeable fluid communication with any of a plurality of different blood pressure measurement devices to enable blood pressure measurements to be performed. If desired, the second adapter can comprise a chamber in direct fluid communication with the cuff opening, wherein the chamber can include, if also desired, at least one screening component for collecting contaminants.

The first adapter (and, if present, the second adapter) enable a cuff of any size and/or type to be quickly and easily individually placed in fluid communication with any of a variety of different blood pressure measurement device so as to facilitate the process of individually taking blood pressure measurements for multiple patients. Thus, in accordance with this exemplary aspect, a truly interchangeable, versatile and easy-to-use blood pressure measurement system is provided.

Optionally, this individual interconnection can be accomplished through the use of at least one hose attachment, the attachment having a first end for connection to the second adapter and a second end for interchangeable individual connection to any of a plurality of blood pressure measuring devices. Thus, interchangeability is provided in at least two important ways. First, in lieu of replacing a cuff/sleeve in order to enable a number of blood pressure measurements to be taken from a single patient via different blood pressure measurement devices or equipment, the system of the present invention merely entails attachment of a second adapter and/or hose. Second, and in a similar vein, the hose and second adapter attachment more easily allow for blood pressure measurements to be taken from multiple patients using the same or different blood pressure measurement equipment and regardless of the size and/or type of cuffs being worn by the patients. Such interchangeability provides valuable time savings and design flexibility as compared to those systems that are currently utilized.

In accordance with this exemplary aspect of the present invention, the cuff can comprise a single sleeve, wherein the interior chamber of the cuff can be formed, by way of non-limiting example, by connecting a first edge of the sleeve to a second edge of the sleeve. Alternatively, the cuff can be formed of two connected sleeves, wherein the interior chamber is defined between the two sleeves. The cuff can assume any size to fit a plurality of patients, including but not limited to sizes that are currently referred to in the art as infant size, pediatric size, small adult size, adult size, large adult size and thigh size, and can be dimensioned to fit either the arm or the thigh of the patient. The cuff size generally is indicated by textual indicia, color indicia, pictorial indicia, or textual and pictorial indicia on the cuff.

Also in accordance with this exemplary aspect, the first adapter can be defined by a socket, the socket being disposed substantially within the exterior surface of the cuff, or a fitting, at least a portion of which protrudes (e.g., in the range of about 1 mm to about 15 mm) from the exterior surface of the cuff by a predetermined distance. The first adapter can include an optional radial seal, which, when present, is in communication with the exterior surface of the cuff and has a diameter greater or smaller than the diameter of the first adapter opening depending on specific attachment conditions. The first adapter can further include a main body that surrounds the radial seal, if present, and is in contact with the exterior surface of the cuff. Optionally, the first adapter can include a flange (e.g., an underlying flange) to enable or facilitate connection of the first adapter to the interior chamber of the cuff, wherein such connection can occur, by way of non-limiting example, by welding (e.g., RF welding, ultrasonic welding, chemical welding, heat welding), bonding or sealing.

In further accordance with this exemplary aspect, the entire first adapter can be made of a single material, or, alternatively, of two or more different materials, wherein "different" means non-identical in one or more regards. By way of example, the main body of the first adapter can be made of a first material and the one or more portions of the remainder of the first adapter (e.g., the rim and/or the ridge of the first adapter) can be made of a second, comparatively more rigid (i.e., less flexible) material. Also, the second adapter can include, if desired, one or more screening components to collect unwanted foreign materials and/or contaminants such as dust and/or debris, wherein the one ore more screening components can be integral to and/or attached to the second adapter.

In yet further accordance with this exemplary aspect, the first and second adapters are releasably connected, whereby the second adapter is at least partially (and, if desired, substantially entirely) rotatable while connected to the first adapter so as to prevent or at least inhibit kinking of hose attached to the second adapter. The releasable connection between the first adapter and the second adapter can be accomplished, by way of non-limiting example, by snap fitting, friction fit, detent action, threaded engagement or by fitting a flange of the second adapter over an elastomeric lip of the first adapter. By way of another non-limiting example, the releasable connection between the first and second adapter can occur by virtue of the second adapter including recesses within which fingers or other protruding portions of the first adapter can fit, e.g., via snap fitting or detent. By way of yet another non-limiting example, the releasable connection between the first adapter and the second adapter can be accomplished by providing the second adapter with a plunger-like mechanism to expand inwardly or outwardly following a predetermined action (e.g., upon the pressing of a button or upon activation of a trigger) in order to hold or release the first adapter in/from tactile communication with the second adapter.

As noted above, and in still further accordance with this exemplary aspect of the invention, the second adapter is adapted for interchangeable, individual connection (i.e., non-simultaneous connection) to any of a plurality of blood pressure measuring devices. Such individual connection can occur by attaching an end of at least one hose to at least one protruding barb of the second adapter or at least one recess defined within the second adapter. The attached hose can have a single lumen or more than one lumen defined therewithin; by way of non-limiting example, the second adapter generally will include one barb or have one recess defined therewithin if the attached hose has a single lumen, whereas the second adapter generally would include two barbs or recesses if the attached hose has two lumens.

If desired, the second adapter can be designed to serve its role as a conduit between the first adapter and the hose attachment while at the same time segmenting flow between these two areas. This can occur, by way of non-limiting example, by designing the second adapter to include a first chamber in direct fluid communication with the opening of the first adapter and a first lumen of attached hose, and to include a second chamber in direct fluid communication with the opening of the first adapter and a second lumen of attached hose. Provision is made of a dividing zone between the first chamber and said second chamber, wherein the dividing zone is effective to minimize fluid communication between said first chamber and said second chamber. The dividing zone can be formed of a first wall in common with the first chamber and a second wall in common with the second chamber, wherein a channel is defined between the first chamber and the second chamber to separate the first chamber and a second chamber by a predetermined distance (e.g., about 1 mm to about 10 mm). The first chamber and the second chamber can have identical shapes or different shapes, wherein an exemplary identical shapes include, but are not limited to, semi-circular and half-elliptical.

In accordance with an exemplary aspect of a blood pressure measurement method of the present invention, blood pressure measurements can be performed using one or more similar or different blood pressure measurement devices by providing a cuff that includes an interior chamber and an exterior surface, wherein a first adapter is substantially disposed within and exposed through the exterior surface of said cuff. The first adapter includes an opening extending into the interior chamber of the cuff to provide direct fluid communication between the exterior surface and the interior chamber of the cuff. The cuff and first adapter generally will have the same features as those described above with respect to the exemplary system of the present invention.

In furtherance of the exemplary method, the cuff is placed in tactile communication with a patient (e.g., by being wrapped around a patient's arm) and a second adapter is releasably connected to the first adapter such that there is direct fluid communication between the first adapter and said second adapter. That, in turn, enables fluid communication between the second adapter and the interior of the cuff/sleeve due to there being direct fluid communication between the first adapter and the interior of the cuff/sleeve. The features of the second adapter and the methods of connecting it to the first adapter also are generally similar to those discussed above with respect to the exemplary system of the present invention.

In still furtherance of the exemplary method, one of a plurality of hoses or hose attachments is selected, wherein the plurality of hoses from which the selection can occur includes at least one hose having a first end, a second end and a single lumen defined therebetween, as well as at least one hose having a first end, a second end and more than one lumen defined therebetween. The first end of the selected hose is then connected to said second adapter and the second end of the selected hose is connected to at least a first piece of equipment to enable a blood pressure measurement to be performed, wherein this first piece of equipment can be any manual or electronic blood pressure measurement device.

This exemplary method enables blood pressure measurements to be interchangeably performed using one or more similar or different blood pressure measurement devices. These measurements can occur, for example, without removing the selected hose that has been attached to the second adapter, such as by disconnecting the second end of the selected hose from the first piece of equipment and connecting the second end of the second hose to a second piece of equipment that is similar or different from the first piece of blood pressure measurement equipment so as to enable a similar or different blood pressure measurement to be performed. Alternatively, these measurements also can occur through removal of the first selected hose that had been attached to the second adapter, such as by disconnecting the second end of the first selected hose from the first piece of blood pressure measurement equipment and then disconnecting the first end of the first selected hose from the second adapter. Thereafter, another of the plurality of hoses is selected and its first end is connected to the second adapter and its second end of said plurality of hoses to a second piece of equipment to enable a separate blood pressure measurement to be performed.

In accordance with another exemplary aspect of the present invention, a kit can be provided that includes or is adapted to include various equipment to enable interchangeable measurement of a patient's blood pressure in a variety of ways and/or through use of a variety of blood pressure measurement equipment or devices. The kit generally will include at least one cuff that is adapted to be wrapped about a limb of a patient, wherein each cuff includes an interior chamber and an exterior surface. The various features of the cuff are generally similar or identical to those described above with respect to the exemplary system of the present invention. The kit generally also will include a first adapter that is substantially disposed within the exterior surface of the cuff, wherein the first adapter includes an opening that extends into the interior chamber of the cuff to provide direct fluid communication between the exterior surface and the interior chamber of the cuff. The various other features of the first adapter also are generally similar or identical to those described above with respect to the exemplary system of the present invention.

The exemplary kit generally also will include at least one (and, optionally, a plurality) of additional adapters, each of which is adapted for connection (e.g., individual, releasable connection) to the first adapter in order to provide direct fluid communication between the first adapter and the at least one additional adapter. The exemplary kit generally will include, as well, a plurality of hoses or hose attachments, each of which has a first end and a second end. The first end of each of said plurality of hoses is adapted for individual connection to one, some or all of the at least one additional adapter, via one or more barbs protruding from or one or more recesses defined within each of the at least one additional adapter. The second end of each of said plurality of hoses is adapted for individual connection to one, some or all of at least one piece of equipment in order to enable a blood pressure measurement to be performed. As described above with respect to the exemplary system of the present invention, each of the plurality of hoses can have a single lumen or more than one lumen defined therein. Optionally, if the hose has two lumens defined therein, one or more of the additional adapters can include a first chamber, a second chamber and a dividing zone as discussed above with respect to the exemplary system of the present invention.

Still other aspects, embodiments and advantages of the present invention are discussed in detail below.

BRIEF DESCRIPTION OF THE DRAWINGS

FIG. 9A is an enlarged view of the attachment of the peripheral bumper to the gage housing of FIG. 9;

FIG. 12 is a side elevation view, in section, of the gage housing of FIG. 11;

FIGS. 12A and 12B are enlarged partial sectioned views of a protective peripheral bumper as attached to the gage housing of FIG. 12;

FIG. 29 is a top view of a cuff with an attached first adapter in accordance with an exemplary embodiment of the present invention;

FIG. 32 is a side view, with cut away of a first adapter releasably connected to the second adapter of FIGS. 31A and 31B;

DETAILED DESCRIPTION

The present invention is herein described with reference to several preferred embodiments, each of which specifically relates to blood pressure measuring apparatus. However, it should be evident to one of sufficient skill in the field that certain other variations and modifications could be made utilizing the inventive concepts described herein, as well as alternate applications other than blood pressure measurement, including use in barometers, pressure vessel indicators, pressure sensitive switches, valves, and literally any industrial or medical device requiring a pressure responsive element. Furthermore and throughout the course of the following discussion, terms such as "upwardly," "downwardly," "upper," "lower," "top," "bottom," "vertically," "horizontally," and the like are used to provide a frame of reference with regard to the accompanying drawings. These terms, however, should not be treated as limiting with regard to the invention as described herein.

In addition, a number of terms are used herein which require definitions. "Gearless" as used herein refers to any movement mechanism disposed within a gage housing which does not include a gear or gear-like element. "Hoseless" as used herein refers to a direct connection between a gage housing and an inflatable sleeve of a pressure measuring apparatus without any intermediate hose or hoses therebetween. Several preferred embodiments of hoseless attachments for a blood pressure measuring apparatus are described throughout the course of the following discussion. "Connected" as used herein refers to state of being reversibly (e.g. releasably) or irreversibly joined in direct contact.

Figure 1:
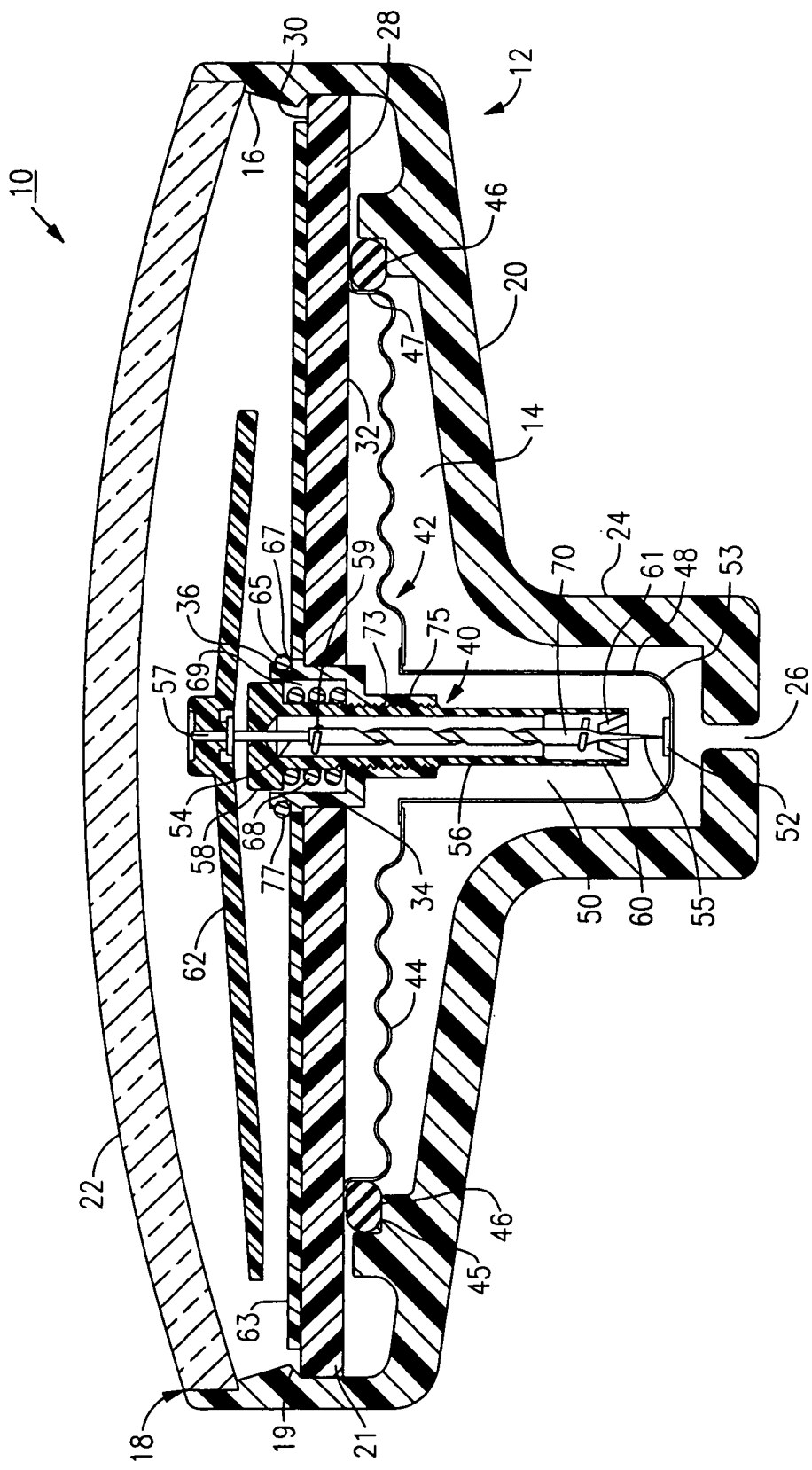
FIG. 1 is a side elevation view, shown in section, of a pressure measuring device according to the present invention.

Referring to FIG. 1, there is shown a blood pressure measuring device or apparatus 10 made in accordance with a first embodiment of the invention. The device 10 includes a substantially cylindrical gage housing 12 having an interior cavity 14 defined by a circumferential inner wall 16, an open top end 18, and a bottom end 20. A viewing window or bubble 22, made from glass, plastic, or other suitable transparent material is attached in a known manner to the open top end 18 of the gage housing 12. The bottom end 20 of the gage housing 12 has a diameter which inwardly tapers down to a narrow downwardly extending portion 24 having a bottom opening 26 serving as an inlet port for admitting a fluid. Preferably, the diameter of the narrow extending portion 24 is about one third of the diameter of the major portion of the housing 12, though it will be apparent from the following discussion that this parameter can be suitably varied depending upon the application.

The interior cavity 14 of the housing 12 is sized for retaining a number of component parts, including a horizontally disposed support plate 28. The support plate 28 is a generally planar member having opposing top and bottom facing sides 30, 32, and a central through opening 34. A press-fitted or otherwise suitably attached or integral sleeve 36 attached to the top facing side 30 of the support plate 28 extends into the central through opening 34 of the support plate 28 and is used for retaining a movement mechanism 40, described in greater detail below.

The circumferential inner wall 16 of the housing 12 further includes a reflexed portion 19 which is sized for supporting an outer edge 21 of the horizontal support plate 28 immediately therebeneath and at a predetermined height within the housing 12. The central through opening 34 is shown as being substantially aligned with the bottom opening 26 of the housing 12, but this particular alignment is not critical to the workings of the present invention and therefore can be varied.

Figure 2:
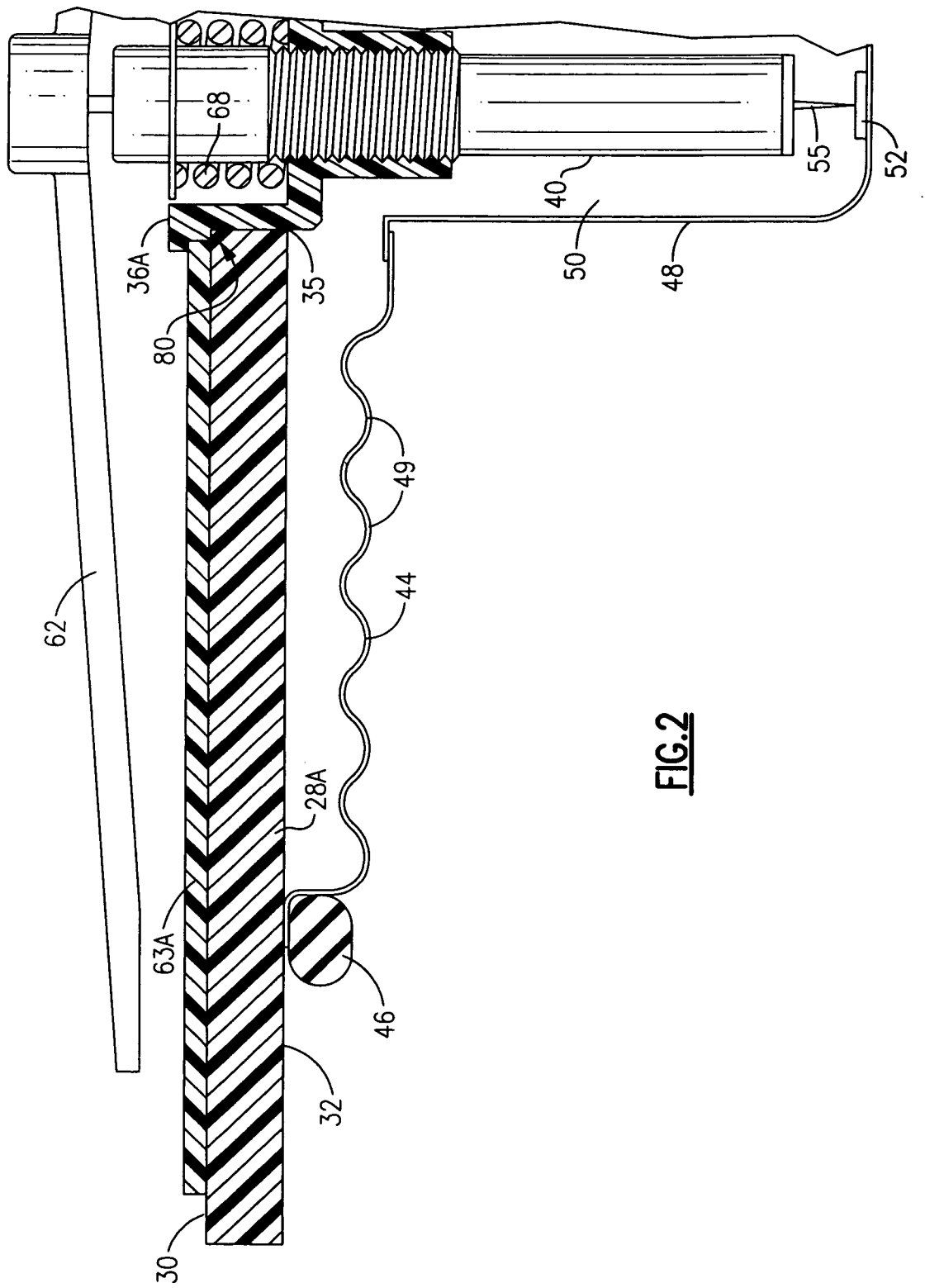
FIG. 2 is an enlarged sectional view of the pressure measuring device of FIG. 1, depicting alternate means for attaching a rotatable dial face in relation to the device.

Referring to FIGS. 1 and 2, a diaphragm subassembly 42 includes a flexible diaphragm 44 which is non-fixedly attached to the bottom facing side 32 of the horizontal support plate 28. The diaphragm 44 is substantially horizontally planar and includes a plurality of wave-like surfaces 49. An outer edge 47 of the diaphragm 44 is clamped by an O-ring 46 disposed on a circumferential ledge 45 extending upwardly from the bottom end 20 of the housing 12. The O-ring 46 not only supports the diaphragm 44 in place, but also provides a fluid tight seal for the bottom of the interior cavity 14.

The centermost portion of the substantially horizontally planar diaphragm 44 includes a downwardly extending section, herein after referred to as the pan 48, which is soldered or otherwise fixed or even integral with the remainder of the diaphragm 44. The pan 48 is a hollow cylindrical section which extends into the downwardly extending portion 24 of the housing 12 when assembled and includes a cavity 50 having a width dimension that is substantially equal to that of the press-fitted sleeve 36. A lower end 53 of the pan 48 includes a interior contact surface 52 that is hardened.

Referring specifically to FIG. 1, the movement mechanism 40 includes an axially displaceable shaft member 54 that is wholly enclosed within a hollow tubular member 56 with the exception of protruding top and bottom ends 57, 55, respectively. A thin flexible ribbon-like spring member 70 is fixedly attached at one end 61 adjacent a bottom end of the tubular member 56 to a fixed portion of the tubular member and at an opposite remaining end 59 to the axially displaceable shaft member 54 around which the ribbon spring member 70 is helically or spirally wound. The hollow tubular member 56 includes a set of external threads 73 extending over an upper portion of the length thereof that engage corresponding internal threads 75 provided in the press-fitted sleeve 36. The ribbon spring member 70 is preferably fabricated from beryllium copper, spring steel, or other similar material.

The hollow tubular member 56 includes an integral top cap portion 58 having a diameter which is larger than that of the remainder of the member, the cap portion having a shoulder which bears against a biasing spring 68 disposed within an annular recess 69 of the press-fitted sleeve 36. The top cap portion 58 and the biasing spring 68 are used to adjust the overall sensitivity of the movement mechanism 40.

When correctly positioned, the majority of the movement mechanism 40 extends beneath the horizontal support plate 28 and into the cavity 50 defined in the pan 48 which is already positioned in the downwardly extending portion 24 of the housing 12. In this position, the extending bottom end 55 of the shaft member 54 is proximate to the hardened contact surface 52.

Still referring to FIG. 1, a dial face 63 having measuring indicia (not shown) is attached to the top facing side 30 of the horizontal support plate 28 through a center opening which is sized to fit over the press-fitted sleeve 36. An O-ring 65 disposed in a slot 67 of the tubular sleeve 36 engages an inner edge of the dial face 63 with an indicating member 62 being mounted to the protruding top end 57 of the shaft member 54. A preferred lightweight indicating member useful in his design is described in U.S. Pat. No. 6,644,123, the entire contents of which are herein incorporated by reference.

In operation, changes in the pressure of incoming fluid (in this example, air) entering the bottom opening 26 of the housing 12 cause corresponding movements of the diaphragm 44. That is, the seal provided onto the outer edge 47 of the diaphragm 44 by the O-ring 46 clamping against the top face of the housing ridge 45 prevents air from further penetrating into the interior cavity 14. Therefore, the increase in pressure causes axial movement of the diaphragm pan 48 with the interior contact surface 52 being caused to push upwardly against the bottom end 55 of the axially displaceable shaft member 54. As a result of the upward movement of the diaphragm 44, the top end of the ribbon spring member 70 is caused to extend relative to the fixed bottom end 61 of the spring member which is fixedly attached to the bottom end of the tubular member 56. This extension causes the shaft member 54 to rotate about its linear axis. The rotation of the axially displaceable shaft member 54 therefore causes a corresponding circumferential movement of the indicating member 62 attached to the top end 57 of the shaft member 54 relative to the measuring indicia (not shown) on the dial face 63.

Zero adjustment of the above pressure measuring device 10 is a relatively simple procedure, as compared with previously known devices. First, the viewing window 22 is removed from the open top end 18 of the gage housing 12. The engagement of the O-ring 65 against the inner edge of the dial face 63 allows the dial face to be freely rotated in relation to the position of the indicating member 62. Sensitivity adjustments can also be made at the top of the device 10 by rotating the top cap portion 58 against the biasing spring 68 within the annular recess 69 of the press-fitted sleeve 36, so as to adjust the sensitivity of the ribbon spring member 70 for a given rotation. A similar mechanism is described in previously incorporated U.S. Pat. No. 6,168,566.

Variations of the above device are possible. For example and referring to FIG. 2 and in lieu of an O-ring, either the dial face 63A and/or the horizontal support plate 28A can be tapered suitably adjacent their center openings relative to a shoulder 80 provided on the tubular sleeve 36A in order to allow the dial face to be rotated without requiring removal. Alternately, the movement mechanism 40 can include a zero adjustment feature as described in U.S. Pat. No. 5,966,829 and U.S. Pat. No. 6,168,566. In passing, it should be noted that FIG. 2 merely illustrates a portion of the overall assembly in order to distinctly facilitate the above discussion.

Figure 3:
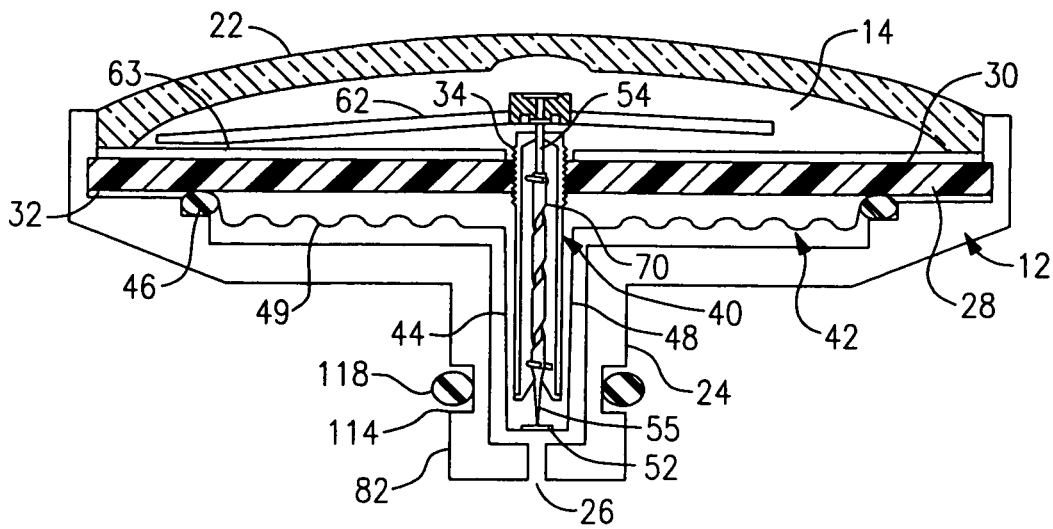
FIG. 3 is a side elevation view, shown partly in section, of a pressure measuring device having a housing according to a second preferred embodiment.

A housing design in accordance with a second embodiment is illustrated in FIG. 3. Similar parts are herein labeled with the same reference numerals for the sake of clarity. As in the preceding, the device includes a gage housing 12 having an interior cavity 14 sized for retaining a diaphragm assembly 42 that includes a diaphragm 44 having a series of wave-like surfaces 49, as well as a downwardly extending portion or pan 48. The device further includes a substantially horizontally disposed planar support plate 28, the housing 12 further having a downwardly extending narrowed portion 24. A movement mechanism 40 is disposed through a central opening 34 defined in the horizontal support plate 28 such that the bottom end 55 of an axially displaceable shaft 54 of the mechanism is disposed in proximity to a hardened contact surface 52 of the pan 48 of the diaphragm assembly 42. The diaphragm 44 in the meantime is attached, but not sealed, to the bottom facing side 32 of the horizontal support plate 28.

A fluid, such as air, entering the gage housing 12 through a bottom opening 26 causes deflection of the pan 48 of the diaphragm 44 against the axially displaceable shaft 54, thereby causing rotation of the shaft by means of an attached ribbon spring member 70, according to the manner previously described.

According to this particular embodiment, the device includes a docking hub 82 that is provided on the exterior of narrow downwardly extending portion 24 of the housing 12, the hub including a circumferential groove 114 which is sized for retaining an O-ring 118 or other similar sealing element. For example, the docking hub 82 can utilize pipe or other form of known threads (not shown). The docking hub 82 provides adequate modification to allow the device to be attached to other existing pressure device housings having pressure sources, for example, those manufactured by Welch Allyn, Inc. of Skaneateles Falls, N.Y., among others. In passing, it should be noted that the position of the bottom opening 26 of the housing 12 is not essential; that is, incoming fluid can enter the housing 12 from either a horizontally or otherwise disposed port, so long as the opening is beneath the seal that is provided by the O-ring 118.

Figure 4:
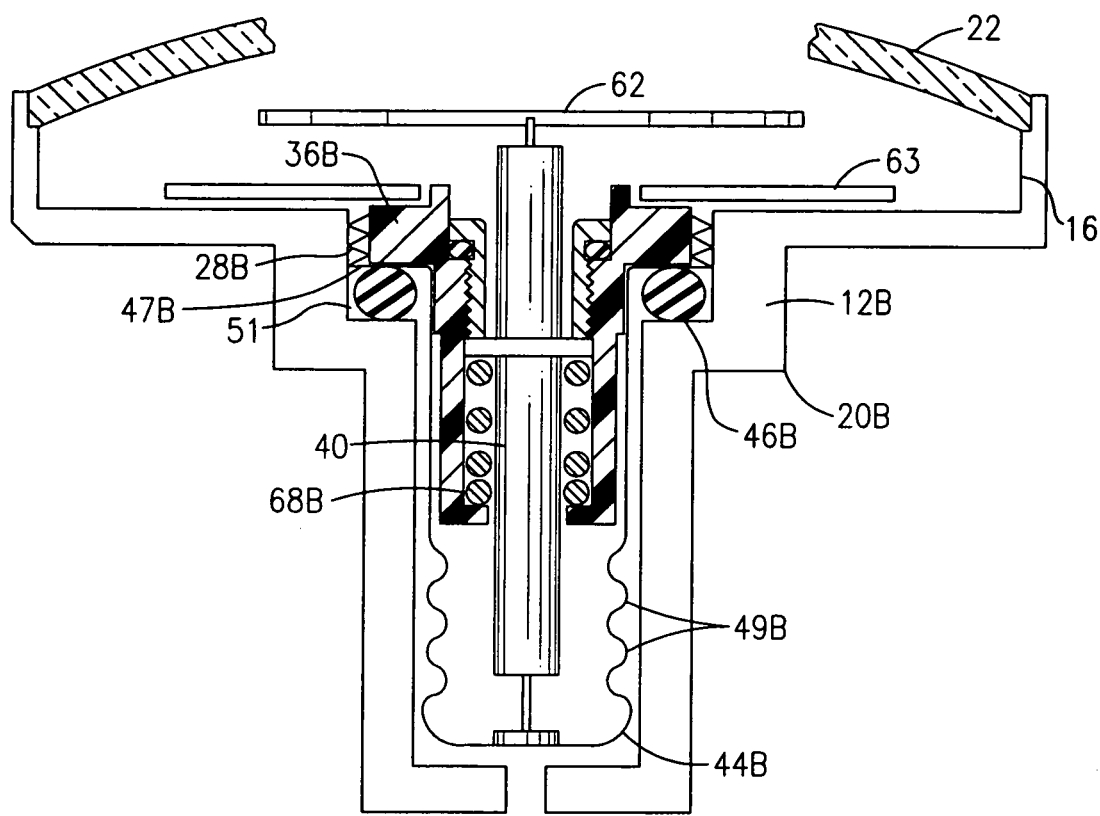
FIG. 4 is a side elevation view, shown partly in section, of a pressure measuring device having a housing according to a third preferred embodiment.

To further illustrate variations and referring to FIG. 4, a third embodiment of a housing 12B made in accordance with the present invention includes a diaphragm 44B, which unlike the preceding embodiments, is a substantially vertical member having an overall width dimension that is considerably narrower than those previously described. As a result, a horizontal support plate is not required, as in the preceding.

As in the preceding embodiments, an outer edge 47B of the diaphragm 44B is sealed using an O-ring 46B or other sealing member which effectively clamps the outer edge to a shoulder of the a press-fitted sleeve 36B. The movement mechanism 40 is disposed essentially through a center opening in a press-fitted sleeve 36B and threaded into engagement therewith. The majority of the movement mechanism 40 is disposed within the cavity defined by the essentially vertical diaphragm 44B, the particular diaphragm of this embodiment having vertically disposed wave-like surfaces 49B. Adjustments to control the sensitivity of the movement mechanism 40 using biasing spring 68B are performed in the manner previously described.

Overall, the housing of the instant embodiment defines a very shallow profile for the upper portion of the gage housing 12B. Though not shown, the bottom end 20B of the gage housing 12B can be used as a docking hub to secure the gage housing into other gage housings (not shown) either as a retrofitted or as a new assembly as previously described. As further described herein, this docking hub can also permit direct hose-free connection between a gage housing and an inflatable blood pressure sleeve.

Figure 5:
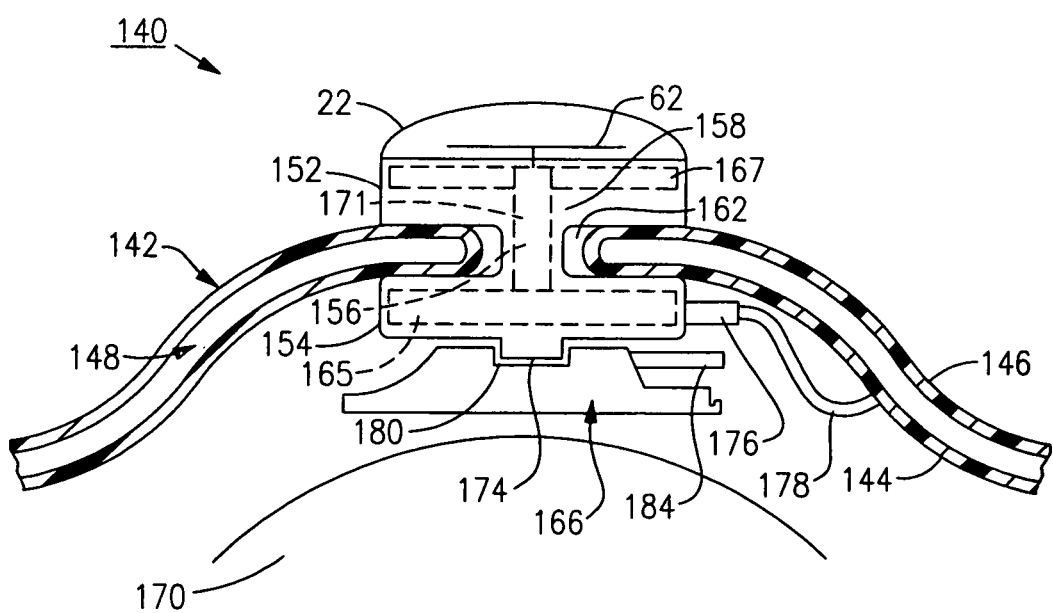
FIG. 5 is a partial sectional view of a pressure measuring device made in accordance with a fourth preferred embodiment as used with an inflatable blood pressure sleeve.

Referring to FIG. 5, a gage or instrument housing 140 formed in accordance with a fourth embodiment of the present invention is herein described in combination with a blood pressure sleeve or cuff 142. For purposes of the present embodiment, the instrument housing 140 is used with a specific blood pressure cuff that is described in greater detail in U.S. Pat. No. 6,036,718, the contents of which are hereby incorporated in its entirety. In brief, the inflatable cuff 142 is manufactured using a pair of sleeve portions 144, 146 that are sealed together using a series of continuous RF (radio frequency) welds to form an integral bladderless structure having an inflatable inner volume 148. In operation, the cuff 142 is then wrapped as conventionally known about the arm 170 (partially shown) or other limb of a patient.

The gage housing 140 includes an upper housing portion 152, a lower housing portion 154, and a connecting intermediate portion 156. The upper and lower housing portions 152, 154 are substantially cylindrical in cross section and have approximately the same dimensions while the intermediate portion 156 has a substantially smaller diameter that is considerably narrower than either adjoining section, thereby defining a configuration resembling a yo-yo. According to the present embodiment, the intermediate portion 156 has a diameter which is approximately one third the diameter of the remaining portions 152, 154, but it will be readily apparent that this parameter can be varied depending on the relative size of the movement mechanism used therein. Each of the above portions 152, 154, 156 are interconnected and hollow, combining to form an interior cavity 158.

According to this embodiment, a horizontal support plate 165 (shown in phantom), is positioned within the lower portion 154 of the housing 140 while a dial face 167 (also shown in phantom) is disposed in the upper portion 152. A movement mechanism 171 (also shown in phantom), which is similar structurally to those previously described, interconnects the dial face 167 and the support plate 165 and is located primarily in the intermediate portion 156.

According to this embodiment, a button-hole like slot 162 is cut both of the inner and outer sleeve portions 144, 146. The edges of the slot 162 are sealed. The above slot 162 provides a button-like retainment for the lower portion 154 of the housing 140 as well as the intermediate portion 156, with the upper portion 152 protruding from the exterior of the cuff 142. A port 176 is connected via a hose 178 to the inflatable inner volume 148 of the cuff 142 which is inflated by a pneumatic bulb (not shown) in a well known manner.

In operation, the device operates similarly to that previously described, except that a detachable stethoscope adapter 166 can also be attached to the bottom of the lower housing portion 154, thereby forming an integral unit. The bottom of the lower portion 154, according to this embodiment, includes an extending attachment portion 174 sized to engage a female connector 180 or other suitable means provided on the adapter 166. All preceding known cuffs require separation between the cuff and the stethoscope. With the overall shallow profile of the above housing 140, use of an adapter 166 permits an interconnection which is highly advantageous.

The stethoscope adapter 166 is a conical member which forms the bell of the stethoscope having connecting ear pieces (not shown) attached to a port 184. In use, the adapter 166 is freely rotatable relative to the housing 140, allowing examination by a patient or care giver to be performed equally well. The overall workings of stethoscopes are commonly known and do not form part of the inventive concepts described hereon.

Figure 6:
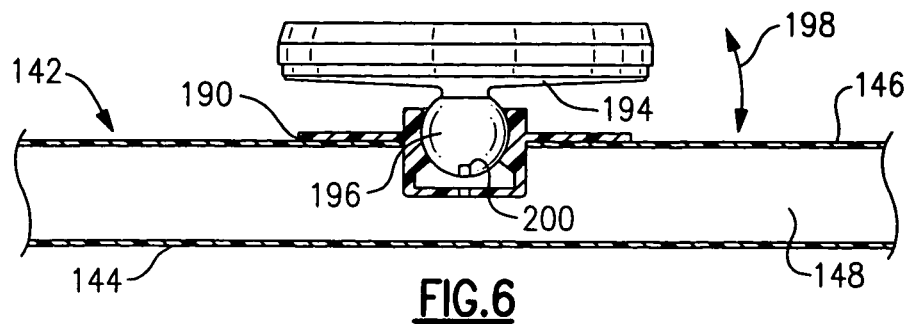
FIG. 6 is a side elevation view, partly in section, of a pressure measuring device made in accordance with a fifth preferred embodiment of the present invention.
Figure 7:
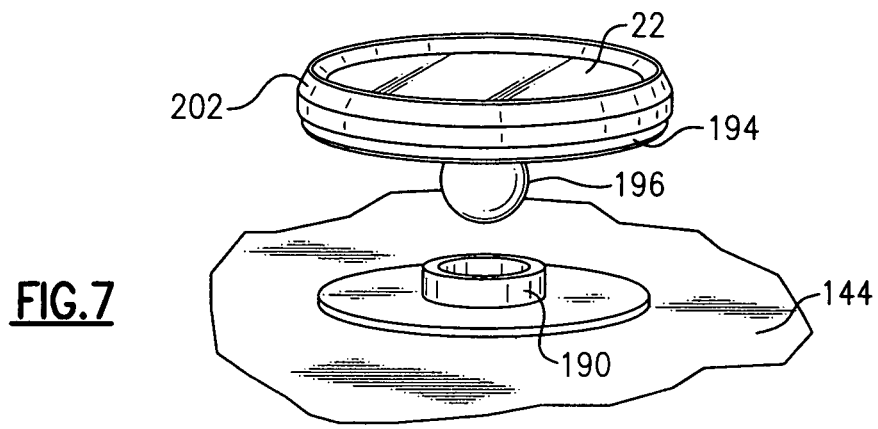
FIG. 7 is an unassembled view of the pressure measuring device of FIG. 6.
Figure 8:
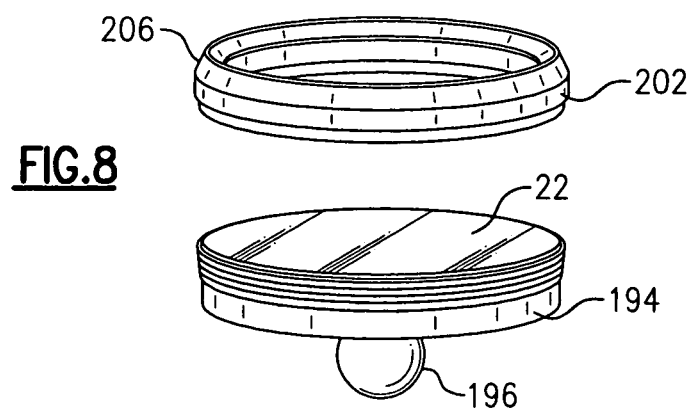
FIG. 8 is a partially exploded view of the housing of the pressure measuring device of FIGS. 6 and 7.

Referring to FIGS. 6-8, there is shown a blood pressure measuring device made in accordance with a fifth embodiment of the present invention. As in the preceding, similar parts are labeled with the same reference numerals for the sake of clarity. This device includes an RF-welded blood pressure sleeve 142 similar to that described in the previously incorporated '718 patent including a pair of sleeve portions 144, 146 which are sealed together to form an integral structure and define an inflatable inner volume 148. The sleeve 142 is sized to be wrapped around the arm or other limb of a patient (not shown) in a manner which is commonly known, and therefore requiring no further explanation. A socket 190 is disposed and fixed within an opening that is provided on the exterior of one of the sleeve portions 144, the socket being sized to receive a mating portion of an instrument or gage housing 194. The instrument housing 194 according to this embodiment is similar to those previously described including a narrowed bottom portion, but in which the bottom portion also includes a ball-shaped engagement or mating end 196. When assembled, the ball-shaped engagement end 196 is fitted within the socket 190 of the sleeve in order to provide a direct fluid and sealed connection therewith, the gage housing 194 being free to pivot relative to the plane of the sleeve 142, about the socket 190, as shown by reference numeral 198.

The engagement end 196 includes an opening 200 that permits fluid communication with the interior of the sleeve 142 wherein fluid (e.g., air) can enter the interior of the gage housing 194, causing corresponding movement of a diaphragm and a contained movement mechanism (not shown in this view), in the manner previously described herein.

Preferably, the viewing window 22 of the housing 194 includes an anti-reflective coating to reduce or substantially reduce glare, with the user (physician or care giver) or patient having the ability to either rotate the housing or to pivot same in order to effectively utilize the instrument and read the dial face. As such, the gage housing 194 can effectively be used in either a right or left-armed patient measurement. A sleeve that further provides this ability with an attached gage housing is described in greater detail below.

Still referring to FIGS. 6-8, the device further includes a rubberized ring-shaped guard or bumper 202 that is press-fitted into engagement about the outer periphery of the gage housing 194, the bumper having a ridge 206 extending a predetermined distance above the viewing window 22. The bumper 202 performs at least two functions; first, and though the present device is ultra-lightweight, the bumper additionally absorbs shock or impact loads when the housing 194 is dropped. Second, the bumper 202 also reduces the likelihood of damage to the viewing window 22.

As described in greater detail in a succeeding embodiment, it should be noted herein that the mating or engagement end of the narrowed bottom portion of the instrument or gage housing need not include a "ball-shape" for accommodation within the sleeve socket 190. Examples are discussed below with reference to FIGS. 9-14.

Furthermore, it should also be apparent that literally any gage housings that include a pressure responsive member can be configured or retrofitted for direct engagement with a blood pressure sleeve without requiring hoses (hoseless) between the housing and the sleeve. Moreover, these housings should not be limited merely to mechanically based gage housings, as described in the foregoing, in that electronic versions can also be retrofitted to the above described sleeve if the electronic version includes or is adapted to include a suitable mating or engagement end.

Figure 15:
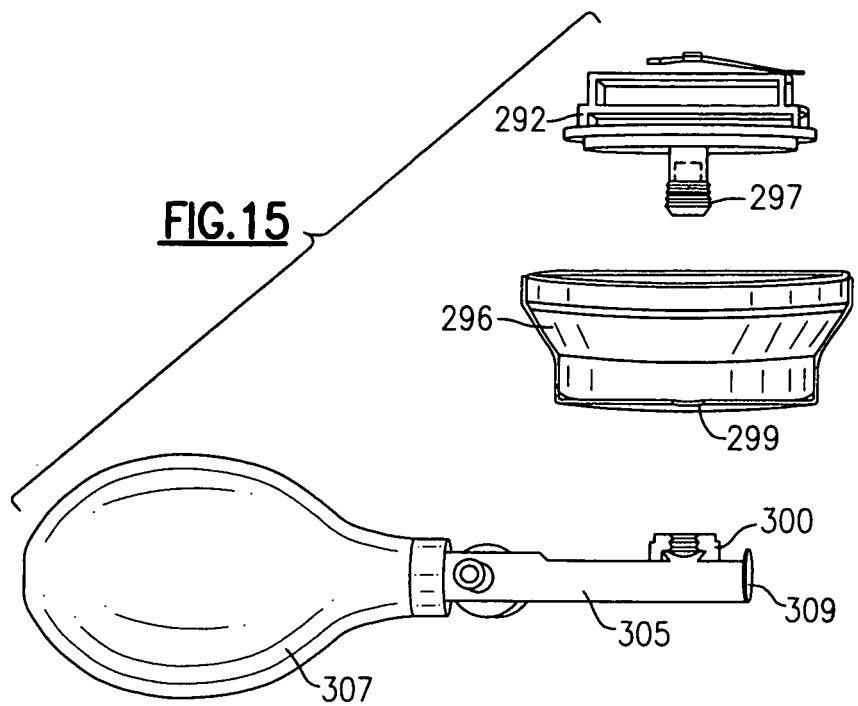
FIG. 15 is a partially exploded view of a conventional blood pressure measuring apparatus.

One example of a prior art mechanical system is partially shown in FIG. 15, and is defined by a gage housing 296 that retains a conventional movement mechanism 292. The movement mechanism 292 includes a threaded end 297 extending through a bottom opening 299 of the gage housing 296 and is received into the mating threaded end of a port 300 of a tubular member 305, the input end of which includes a pneumatic bulb 307. In use, the output end 309 of the tubular member 305 receives a hose (not shown) that extends to a coupling of a blood pressure sleeve (not shown).

Figure 16:
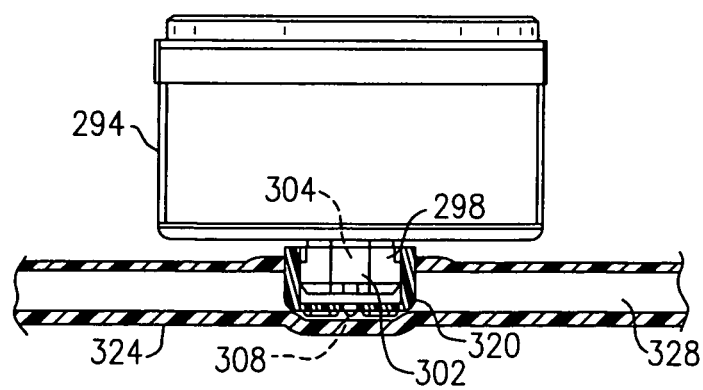
FIGS. 16 and 17 are side elevation views, partly in section, of conventional gage housings which have been configured for direct attachment to an inflatable blood pressure sleeve.
Figure 17:
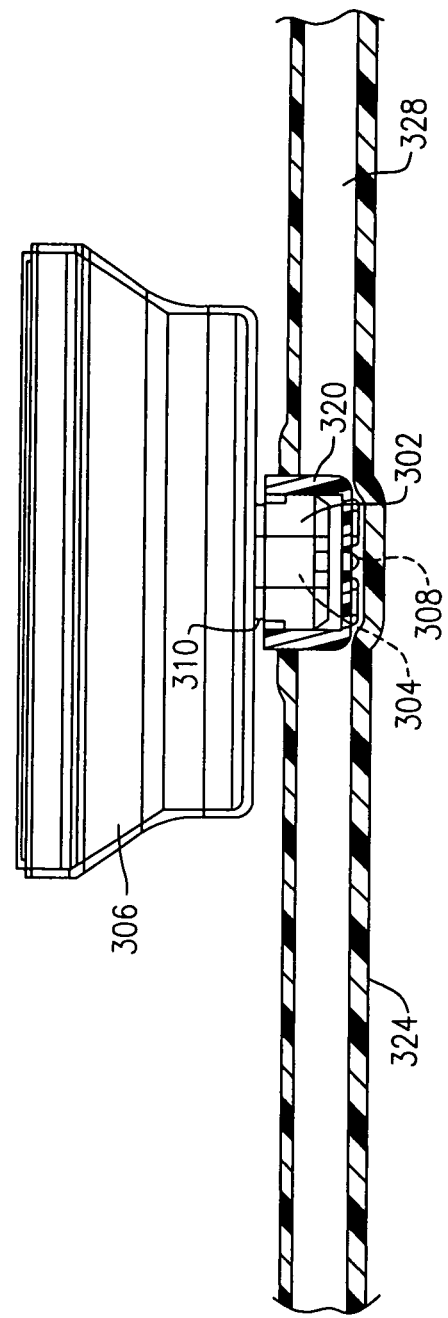

Referring to FIGS. 16 and 17, respectively, a pair of known mechanical gage housings 294, 306 are shown that can be interconnected to a blood pressure sleeve 324 in a manner similar that previously described. Each of these conventional housings 294, 306, similar to those of FIG. 15, are less compact than those which have been expressly detailed, mainly because of the intricacy and sizing of the movement mechanism that is contained therein. Each of the gage housings 294, 306, however, do commonly contain a threaded engagement end or inlet port 298, 310, that permits fluid communication between the housing interior and the pneumatic bulb 307, FIG. 15. The pneumatic bulb 307 is attached using a hose (not shown) to the inlet port. As noted previously, any gage housing having an engagement or inlet end and including literally any form of movement mechanism can be reconfigured according to the present invention for hoseless interconnection with an inflatable sleeve. A number of additional examples are now described to further illustrate this point.

According to the present invention and in order to retrofit the gage housings 294, 306, the end of the threaded inlet port 298, 310 can be covered with an adapter or cap 302 which is sized for sealing engagement within a socket 320 provided in an inflatable blood pressure sleeve 324. The cap 302 and the socket 320 each include respective openings 304, 308, which as shown in FIGS. 16 and 17 upon attachment to the inflatable sleeve 324, permits direct fluid communication between the interior 328 of the sleeve 324 and the interior of the housing 294, 306, the housing being preferably snap-fitted to the sleeve. As a result, there is no need to include the hoses which are essential to the prior art assembly of FIG. 15, thereby greatly simplifying the use of even conventional devices by permitting direct, hose free connection to an inflatable blood pressure sleeve.

Referring to FIGS. 20-28, another series of preferred embodiments are herein described to better depict the versatility achieved by the present invention. All of the preceding embodiments have referred to so-called mechanical hoseless connections, that is, each of the gage housings have included a movement mechanism which is mechanical in nature. As noted above, however, any form of movement mechanism that is capable of producing a result based on a change of pressure can be utilized.

Figure 20:
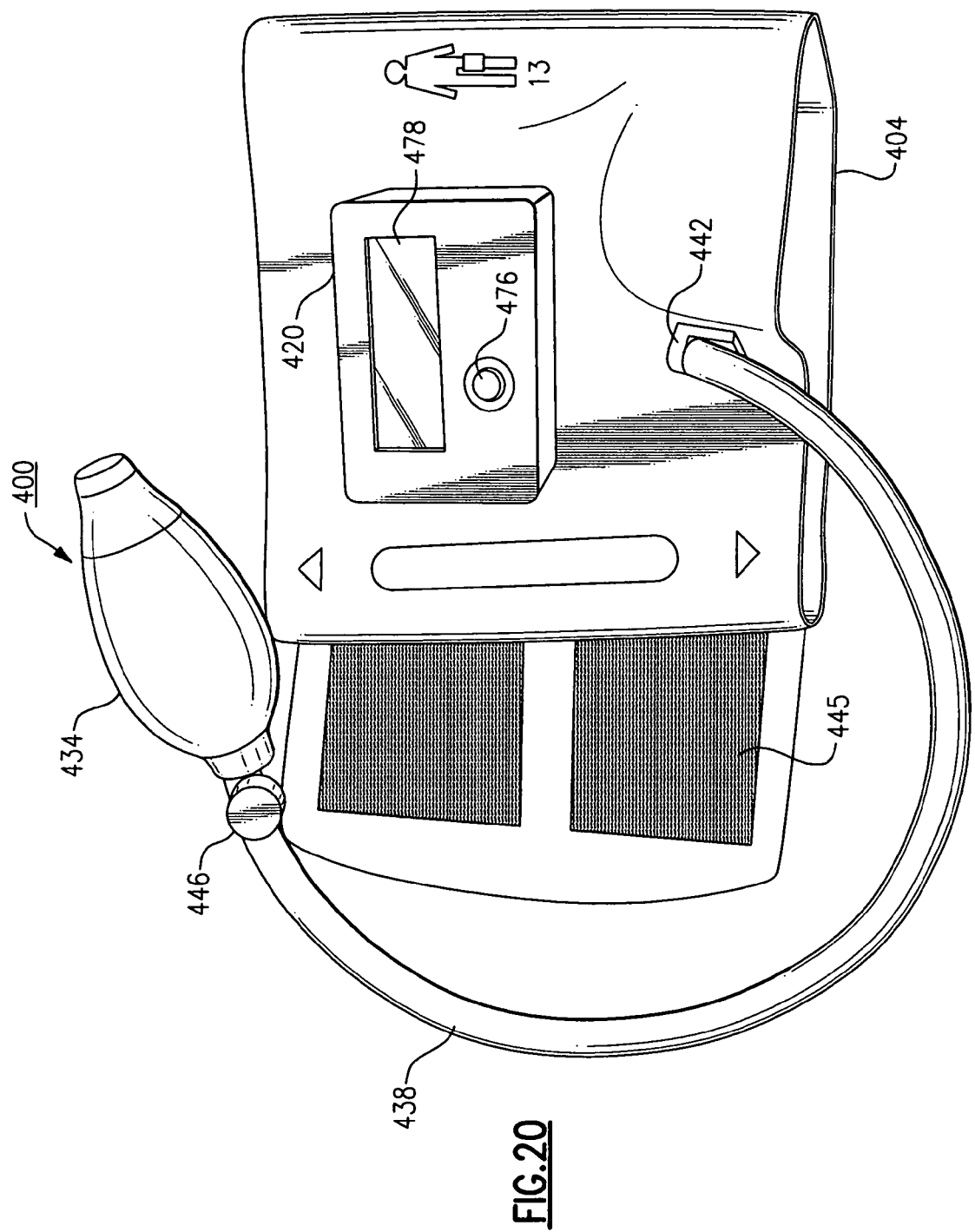
FIG. 20 is an assembled top perspective view of a blood pressure measuring apparatus in accordance with another preferred embodiment of the present invention.
Figure 21:
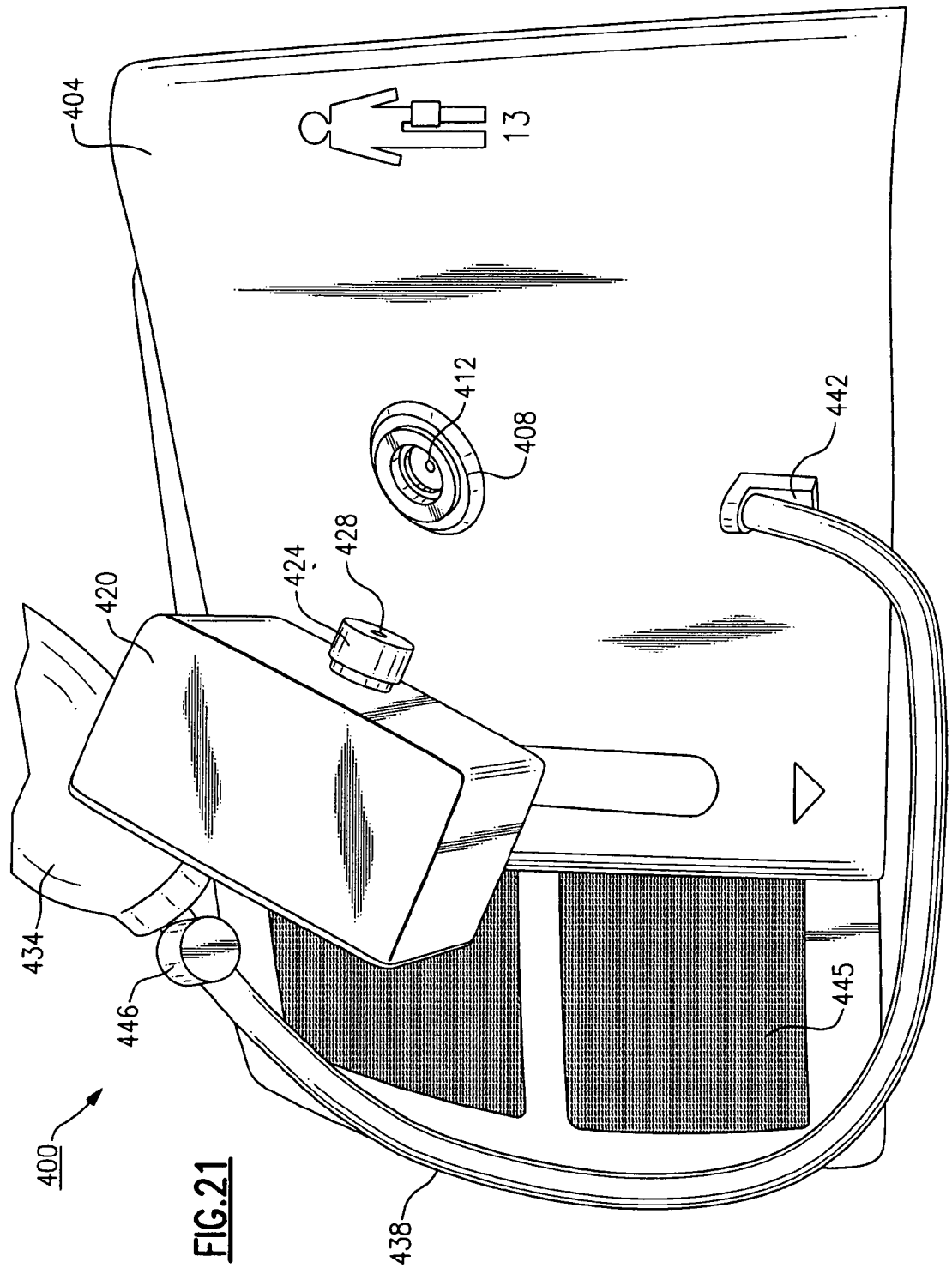
FIG. 21 is the top perspective view of the blood pressure measuring apparatus depicted in FIG. 20 with the electronic gage module removed from the sleeve.

To that end and first referring to FIGS. 20 and 21, a blood pressure measuring assembly 400 includes a blood pressure sleeve 404 such as previously described which is bladderless, such as described in U.S. Pat. No. 6,036,718, the sleeve including a port 408 containing a small opening 412 that maintains fluid communication with the interior (not shown) of the sleeve. The port 408 permits engagement to an electronic gage module or housing 420 having a number of interior component parts, that are described in greater detail below, as well as a proximal end 424 that is sized to permit a direct releasable connection with the port without the need or requirement of additional hoses therebetween, the proximal end including an aligned end opening 428. The sleeve 404 is inflated by means of a pneumatic bulb 434 that is tethered by a hose 438 to a coupling 442 provided on the sleeve, the coupling having an opening extending into the interior of the sleeve. A bleed valve 446 adjacent the pneumatic bulb 434 assists in the deflation of the sleeve 404 in a manner conventionally known. The sleeve 404 is bladderless, can be securably wrapped about a limb of a patient (not shown) by means of hoop and loop fastener portions 445.

Figure 22:
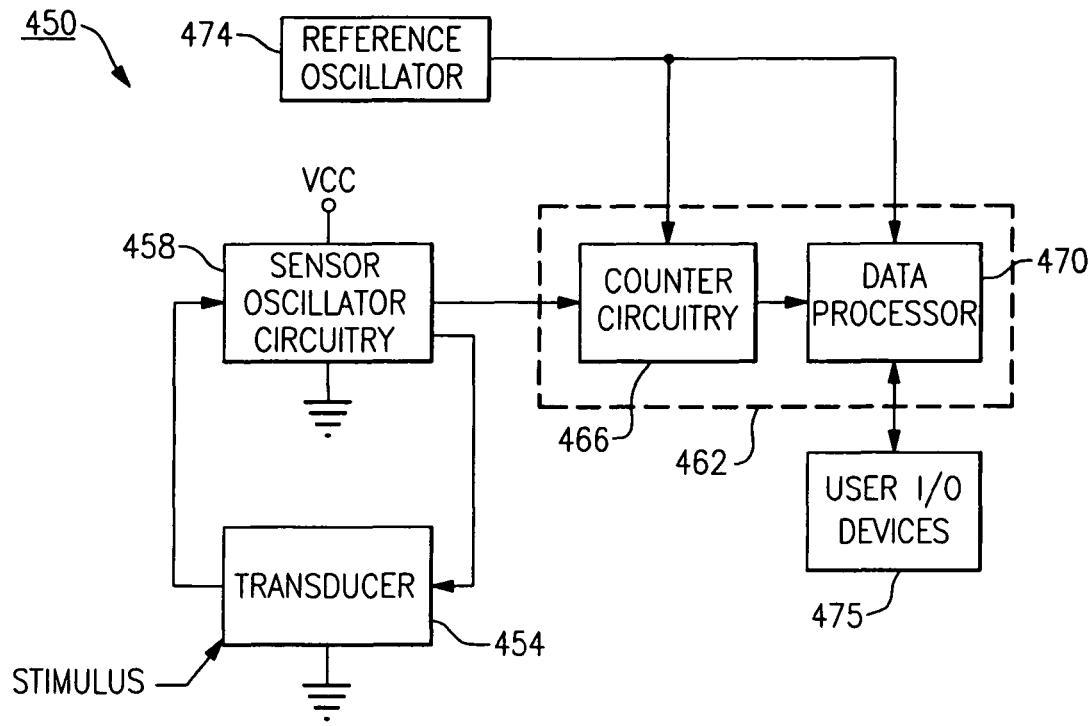
FIG. 22 is a functional block diagram of a capacitance transducer for use in the electronic gage module of the blood pressure measuring apparatus of FIGS. 20 and 21.

Referring to FIG. 22, a block diagram illustrates the primary componentry, in this instance, a capacitance transducer assembly 450 of an electronic pressure gauge contained within the electronic gage module 420. This transducer assembly 450 generally includes a capacitance pressure sensor transducer 454 that is responsive to a stimulus, (in this instance, the stimulus is the input of fluid into the interior of the electronic gage module from the sleeve 404, FIG. 20), the transducer being operatively connected to an oscillator circuit 458. A measurement and processing circuit 462 is connected to the output of the oscillator circuit 458. The measurement and processing circuit 462 includes a counter circuit 466 that is connected to a data processor 470, each of the latter being connected to a reference oscillator 474, the data processor being connected to user I/O devices 475. In this instance, the I/O devices 475 include an actuable button 476, FIG. 20, provided on the exterior of the module as well as a display 478, FIG. 21.

In terms of general operation, essentially the dynamic portion of transducer 454 is a variable capacitor. As the measured environmental parameter changes (the entering fluid pressure), the capacitance changes. The oscillator circuit 458 converts this capacitance change into an AC signal. The processor 470 converts the measured frequency into the parameter (e.g., pressure) measurement and the measured parameter is then displayed upon the display 478.

Figure 23:
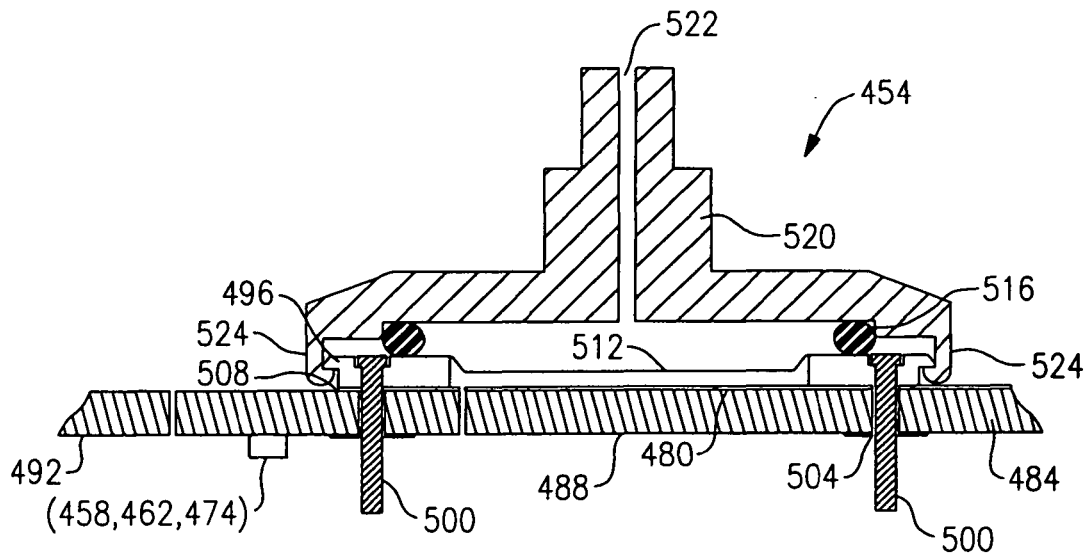
FIG. 23 is a cross sectional view of a capacitance sensor assembly used that can be used in the electronic gage module of FIGS. 20-22.

Referring to FIG. 23, a preferred capacitance sensor transducer 454 for use in the above assembly 450 is described in greater detail for exemplary purposes, the transducer including a capacitance sensor that includes a metallic conductor layer 480 formed on a surface of a circuit board 484. A ground conductor layer 488 is disposed on the opposite surface 492 of the circuit board 484, that also includes a dielectric material, disposed between the conductor layer 480 and the ground conducting layer 488. A metal ring 496 is connected to the circuit board 484 by pins 500, that are inserted through a ring conductor 504. The metal ring 496 receives structural support from a support plate 508 that is disposed between the circuit board 484 and the metal ring 496. The support plate 508 causes the conductor layer 480 and the support plane of the metal ring 496 to be co-planar, thereby reducing mechanical tolerance stack-up. A metallic diaphragm 512 is coupled to the circuit board 484 as sandwiched between the metal ring 496 and an O-ring 516. Therefore, the metallic diaphragm 512 is disposed over the circuit board 484 and is juxtaposed relative to the conductor layer 480 to form a variable capacitor. The metallic diaphragm 512 is held in place by the O-ring 516 which is pressed against the diaphragm and metal ring 496 by a snap-on cap 520. The snap-on cap 520 includes a port 522 aligned to permit fluid to enter same as stimulus as well as multiple snaps 524 that fit over the edge of the metal ring 496. A set of electronics; more particularly, an oscillator circuit 458 and a measurement and processor circuit 462 as well as a reference oscillator 474, for the sensor are mounted to the underside 492 of the circuit board 484.

Figure 24:
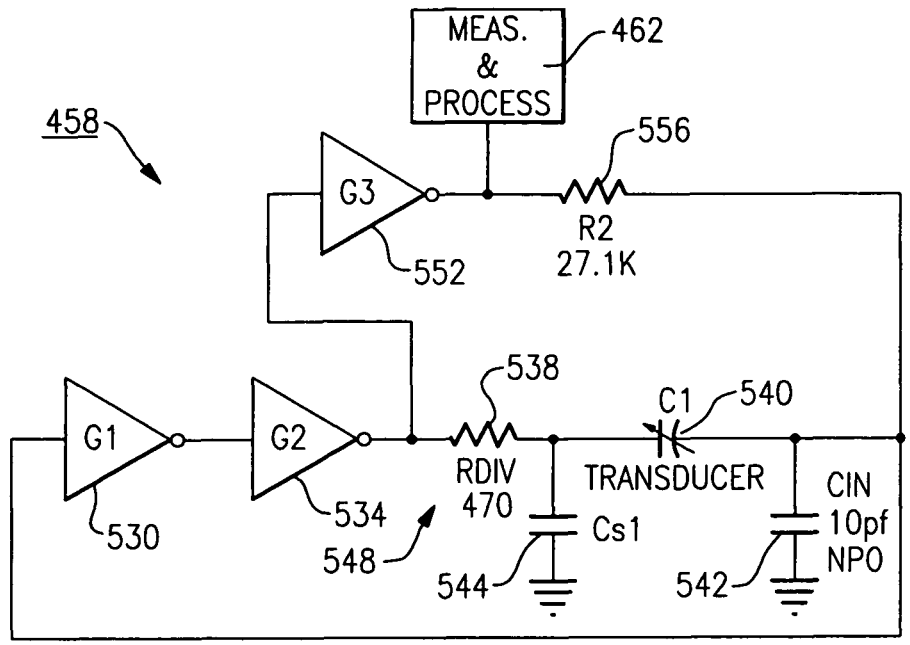
FIG. 24 is a preferred oscillator circuit for use in the electronic gage module of FIGS. 20-23.

Referring to FIG. 24, a schematic of a preferred oscillator circuit is herein described. This circuit 458 includes a first loop having an inverter gate 530, inverter gate 534, resistor 538, and a capacitive sensor 540, such as just described in FIG. 23, in series. An optional capacitor 542 is connected between the input of the inverter gate 530 and ground. An optional capacitor 544 is connected between the output of the resistor 538 and ground. The capacitor 542 and capacitor 544 are in parallel with stray capacitances resulting from the construction of the sensor 450 and the proximity of the oscillator 458 on the circuit board 492 to the ground conductor. A low-pass filter 548 is formed by the series resistor 538 in combination with the capacitor 542, capacitor 544 and the stray capacitances referred to above. The oscillator circuit 458 also includes a second loop in parallel with the resistor 538 and capacitance transducer 540. The second loop includes an inverter gate 552 in series with a resistor 556. The output of the oscillator circuit 458 is connected to the measurement and processing circuit 462.

This oscillator circuit 458 is a type of RC relaxation oscillator wherein the dynamic portion of the oscillator circuit 458 is the capacitance transducer 540, as described above. Additional details concerning the above sensor and transducer assembly, including the above referred to oscillator circuit, can be found in U.S. Pat. No. 6,828,801, the entire contents of which are herein incorporated by reference.

Figure 25:
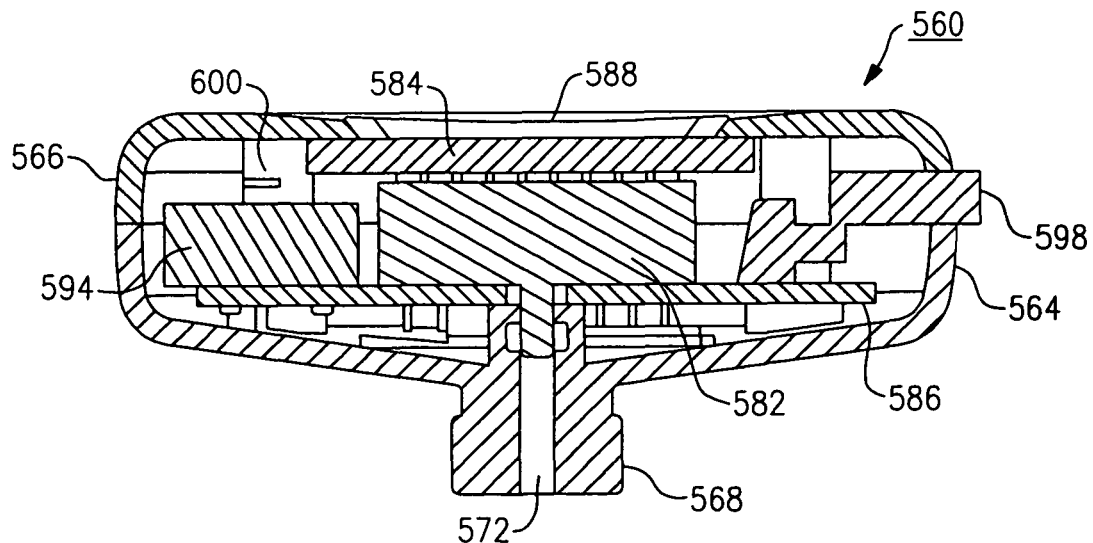
FIG. 25 is a cross-sectional view illustrating the interior of another electronic gage housing in accordance with the present invention.
Figure 26:
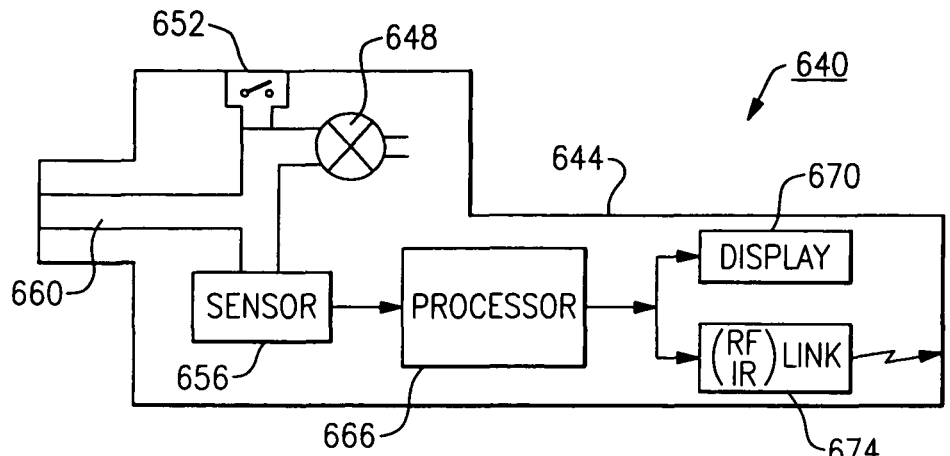
FIG. 26 is a functional block diagram of another configuration for use in the electronic gage module of FIGS. 20-25.
Figure 27:
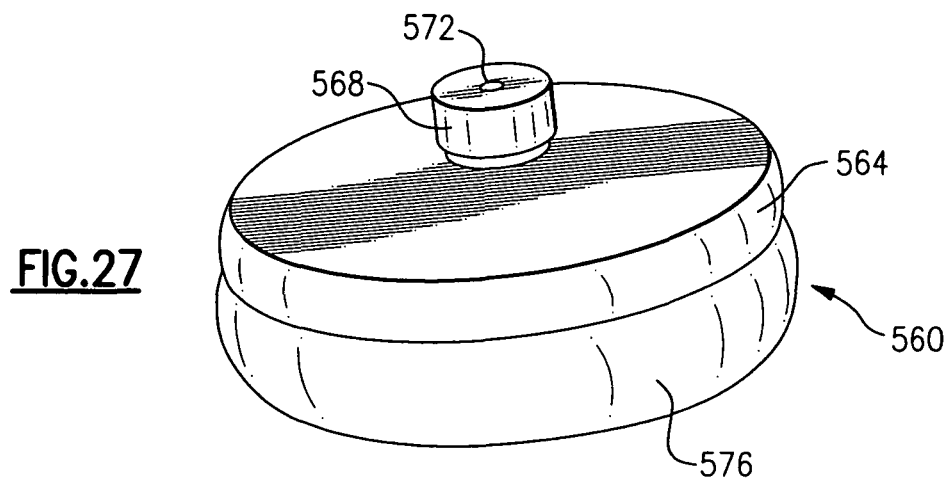
FIGS. 27 and 28 depict bottom and top perspective views, respectively, of another electronic gage module in accordance with the present invention.
Figure 28:
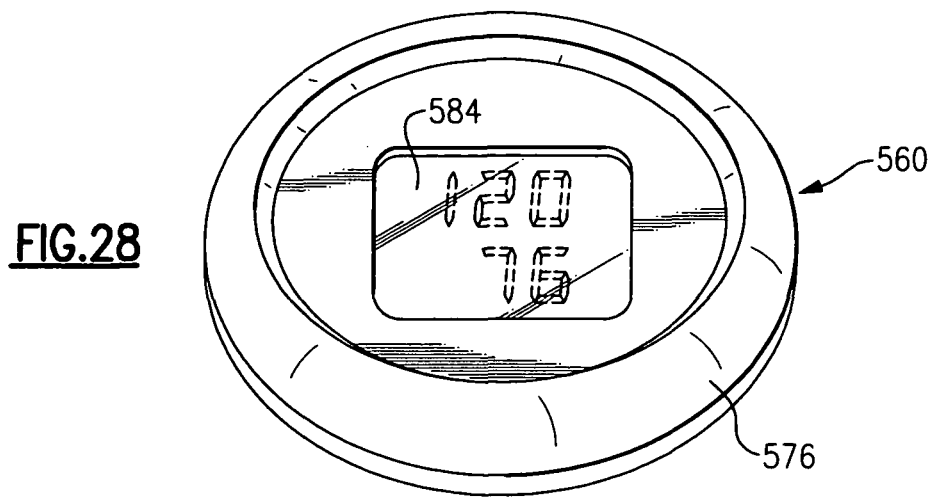

A cross-sectional view of the components as stored within the interior of another version of another suitable electronic gage module 560 are shown in FIG. 25. It should be readily apparent that this module is exemplary, and that modifications and variations can be found, for example, in U.S. Pat. Nos. 5,323,782 and 5,316,006. Exterior views of this module 560 are depicted in FIGS. 27 and 28, the module having an ovate geometry that is defined by a housing body 564 which includes a upper or major housing section 566 and a proximal engagement section 568 that is sized to be sealingly and releasably fitted into a port or socket 408 of a blood pressure sleeve 404, such as that shown in FIGS. 20 and 21, and in the manner previously described. The proximal engagement section 568 includes an end opening 572 extending into the interior of the module 560 and particularly to a contained capacitance transducer sensor assembly 582, coupled to a circuit board 586, the sensor assembly having a metallic diaphragm (not shown in this view) and operative in a manner as previously described. The interior of the module 560 further includes relevant circuitry as well as a processor 594 interconnecting the above components including a display, such as an LCD 584 that positioned relative to a viewing window 588. Each of the above are interconnected in the manner previously described to an input means such as an ON/OFF button 598, disposed on the upper housing section 566 of the module 560, each being powered by batteries 600.

The exterior of the housing body 564 further includes a peripheral bumper 576, shown in FIGS. 27 and 28 only, that protects the upper housing section 566 when dropped. The bumper 576 is preferably raised above the LCD 584. Within the module 560 are a number of components including the capacitance transducer sensor assembly 582, similar to that previously described, Referring to FIG. 26, an alternate design for an electronic gage housing or module 640 is depicted wherein fluid enters a housing body 644 as from a sleeve (not shown) regulated by a valve 648 or pneumatic bulb (not shown) attached to a pressure-sensitive switch 652. The sensor 656, such as the preceding capacitive sensor is operatively connected to receive the fluid incoming stream through a port 660, the sensor being controlled by circuitry retained with a miniature processor 666. Blood pressure readings are then calculated by the processor 666 for either output by a display 670 or the pressure information signal is alternately converted through appropriate means into digital values that can be transmitted wirelessly by means of a RF or IR based link 674 to a remote site (not shown).

In passing, it should further be noted that though an RF welded or bonded inflatable sleeve is described throughout, other forms of inflatable sleeves can be utilized embodying the central concepts of the present invention, including both bladderless sleeves and sleeves having bladders. In addition, other forms of systems can be employed other than the capacitance sensor described herein. For example, a strain gage including a silicon pressure sensor could be employed in combination with an analog amplifier and an A/D converter to produce a digital signal. Alternately, a diaphragm could be employed in combination with a pair of ultrasonic transducers to produce a time delay signal. According to yet another example, an optical version could be contemplated using a laser and a diffraction grating in which interference fringe counts could be used as a determining means.

Still according to another alternative, a magnetic based system could be utilized in combination with a diaphragm and an LVDT. A MEMs-based version is also possible within the ambits of the invention provided the packaging is suitably convenient for sleeve attachment. Each of the foregoing can be used with a diaphragm though use of a diaphragm may also not be required. For example, a Bourdon tube could be employed in lieu of a diaphragm. Alternately, a spring and a rolling seal piston could be substituted for the diaphragm, indicating the myriad of potential uses and applications.

Figure 9:
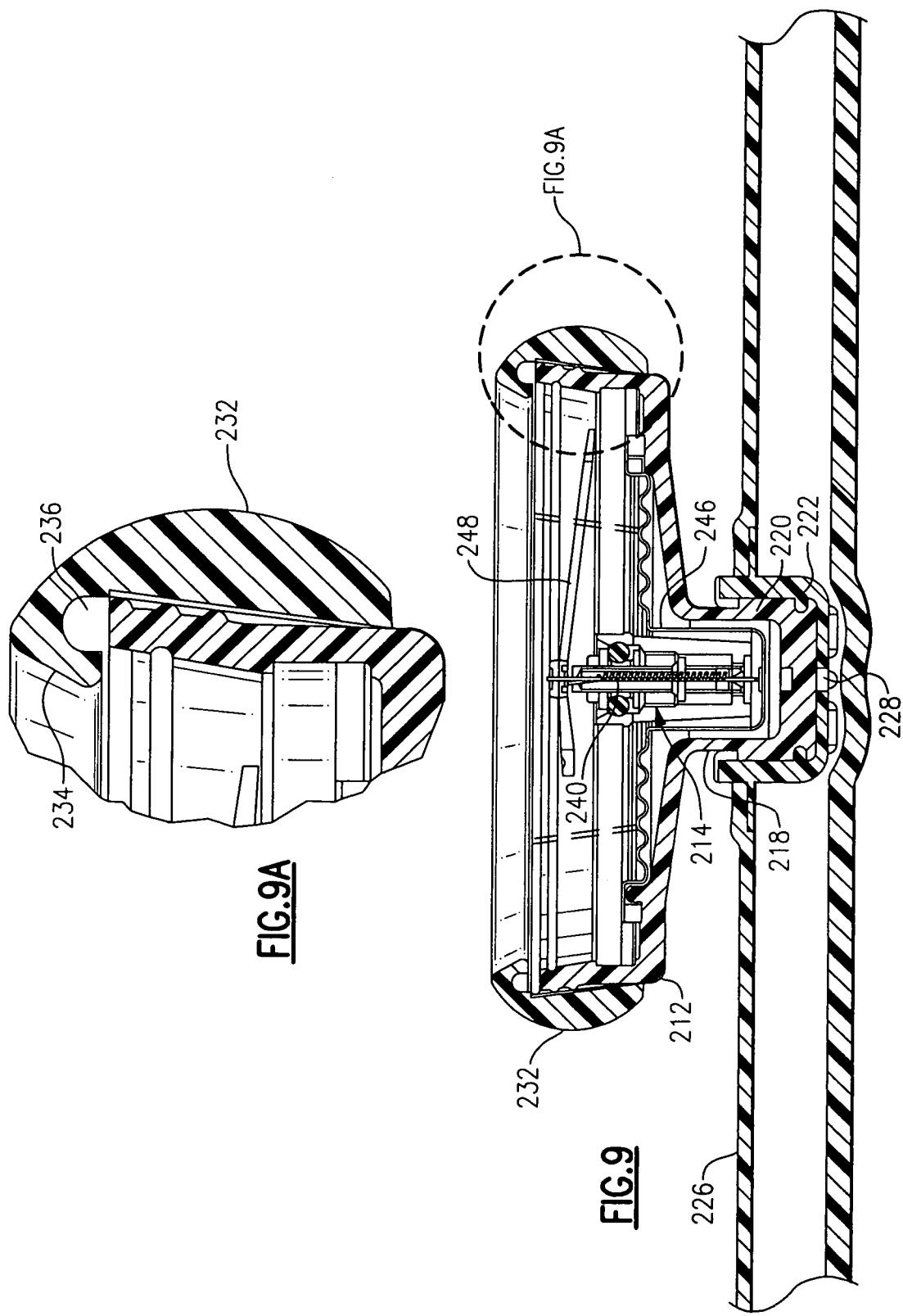
FIG. 9 is a side elevation view, in section, of a gage housing made in accordance with a sixth embodiment of the present invention.
Figure 10:
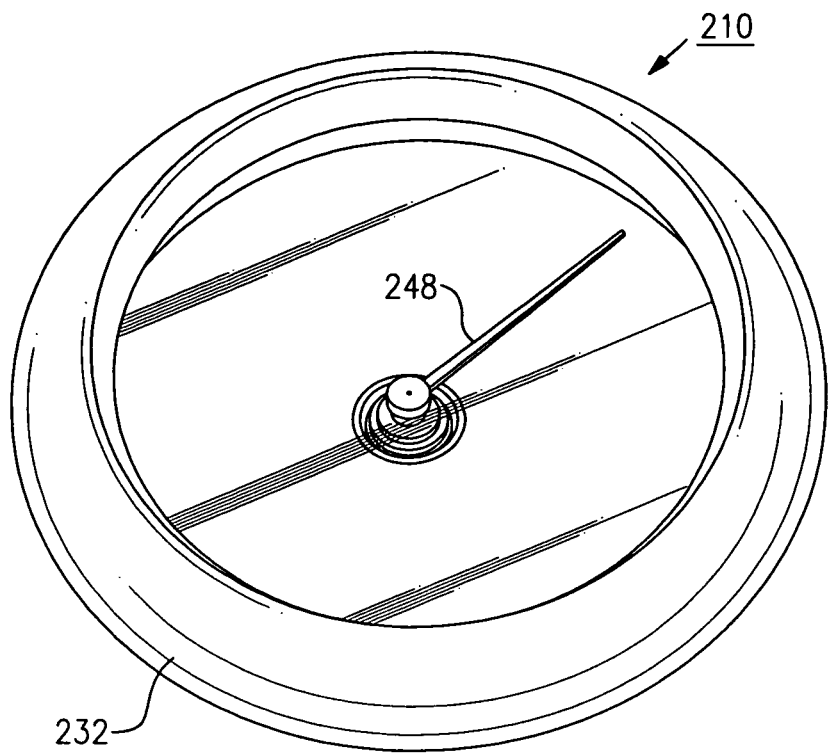
FIG. 10 is a top perspective view of the gage housing of FIG. 9.
Figure 11:
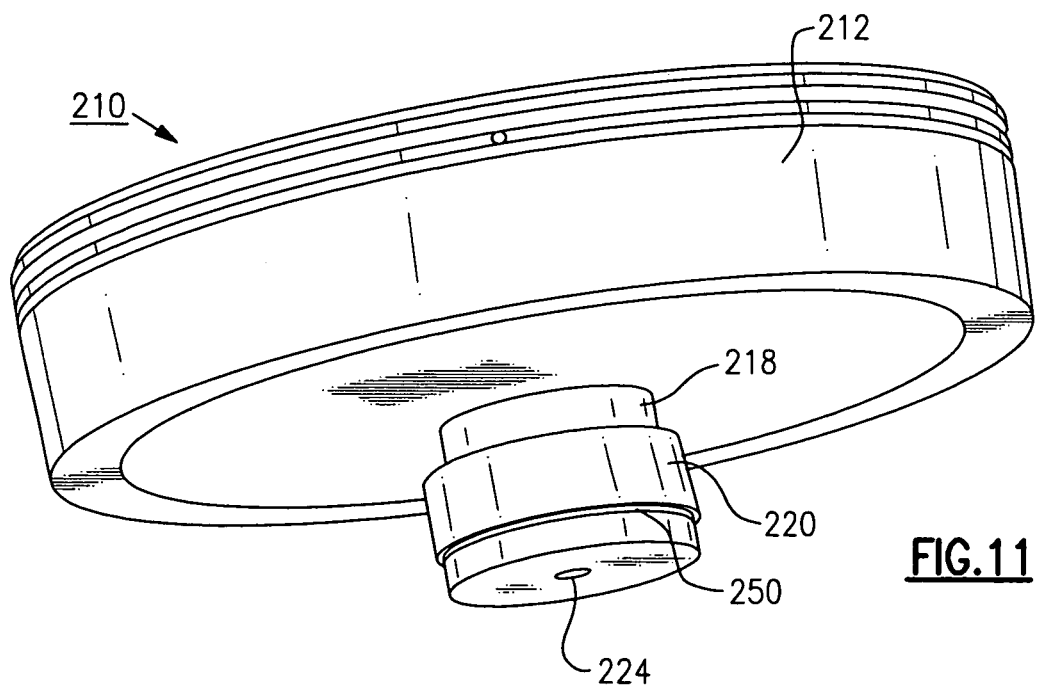
FIG. 11 is a side perspective view of a gage housing made in accordance with a seventh embodiment of the present invention.
Figure 13:
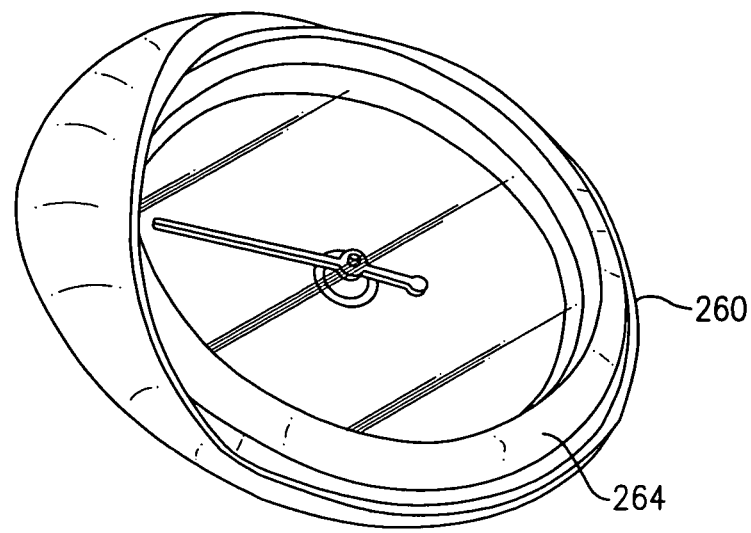
FIG. 13 is a top perspective view of the gage housing of FIG. 12.
Figure 14:
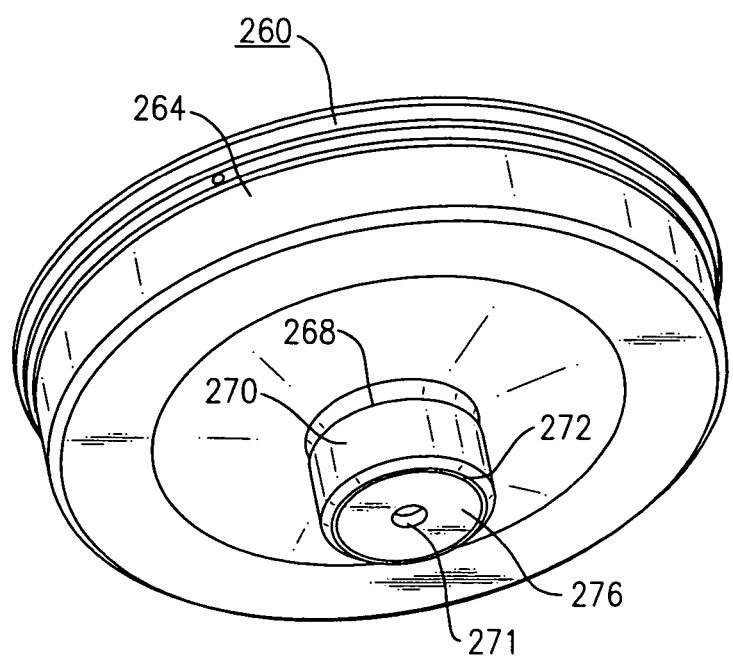
FIG. 14 is a bottom perspective view of the gage housing of FIG. 12 having a shock resistant feature made in accordance with another embodiment of the present invention.

Referring to FIGS. 9-11, there is shown a gage or instrument housing 210 according to a sixth embodiment of the present invention. As in the preceding, the gage housing 210 is used in connection with a blood pressure measuring device and includes an upper housing portion 212 which retains a movement mechanism 214 and a narrowed lower portion 218 having a mating or engagement end 220 which is sized to engage a generally cylindrical socket 222 formed in a sleeve portion of a bladderless blood pressure cuff or sleeve 226. Unlike the preceding embodiment, the mating end 220 of the narrowed lower portion 218 is also generally cylindrical in cross section, the end similarly including an end opening 224, shown in FIG. 11, which permits fluid communication with the interior of the blood pressure cuff 226 via a corresponding opening 228 also formed in the socket 222, thereby forming a fluid inlet port.

The upper housing portion 212 of the gage housing 210 and the contained movement mechanism 214 are similar to those previously described. That is, the movement mechanism 214 includes a helically wound thin ribbon spring 240 which is attached at one end to an axially displaceable shaft member and at a second end to a tubular sleeve member in the manner described above. Changes in pressure of the cuff 226 cause fluid to enter the narrowed lower housing portion 218 through the end opening 224, affecting a contained diaphragm 246 and causing the axially displaceable shaft member to be translated upwardly, resulting in rotation of the shaft member against the biasing of the ribbon spring 240 and circumferential movement of an indicating member 248, attached to a protruding top end of the shaft member, relative to a dial face.

The mating end 220 of the narrowed lower housing portion 218 can include a circumferential channel or notch 250, that is most clearly shown in FIG. 11. The circumferential channel 250 provides a discontinuous path for shock and impact loads and, therefore, effectively cushions the contents of the gage housing 210 including the movement mechanism 214, from shock or impact loads such as when the housing 210 lands on the narrowed lower portion 218.

According to this embodiment and as most clearly shown in FIGS. 9 and 10, and to further insulate the housing 210 from damage due to shock or impact loading, a rubberized peripheral guard or bumper member 232, sized to fit over the exterior periphery of the upper housing portion 212 is press fitted into engagement therewith. The guard member 232 is similar to that previously described above in that the entire periphery of the upper housing portion 212 is covered, the guard member including a stepped portion 234, shown in FIG. 9A, which extends over the top of the upper housing portion, including the viewing window, and defines an air gap 236 along the outer circumferential edge thereof. The air gap 236 provides a discontinuous path for any impact loads which can occur if the gage housing 210 lands awkwardly.

Variations of the above embodiment of FIGS. 9-11 are possible. For example, and referring to FIGS. 12-14, there is shown a gage housing 260 according to a seventh embodiment of the present invention. The gage housing 260 also includes an upper housing portion 264 and a narrowed lower housing portion 268 having an engagement end 270 which mates with a socket 222 which is formed in blood pressure sleeve 226. The upper housing portion 264 according to this embodiment is defined by a substantially elliptical cylindrical cross section as opposed to the preceding embodiments in which the upper housing portions are substantially circular cylinders. It should be noted that other shapes or geometries could be contemplated. According to this embodiment, a circular face groove 272 provided in the bottom surface 276 of the engagement end 270 provides a similar function to the circumferential channel 250, FIG. 11, with regard to shock or impact loads applied to the housing if dropped or otherwise acted upon.

Otherwise, the engagement end 270 similarly engages the socket 222 of the sleeve 226, the gage housing 260 retaining a movement mechanism (not shown) as previously described. The engagement end 270 includes an end opening 271 which permits hoseless fluid communication with the sleeve 226, also as previously described, through a socket opening 228 which extends to the sleeve interior.

According to the instant embodiment, a rubberized guard member 280 is press fitted over the exterior periphery of the upper housing portion 264, the guard member according to this embodiment including a radially extending portion 284 which when attached extends from the outer edge of the elliptically shaped upper housing portion 264 and similarly provides a cushioning air gap 286 which creates a discontinuity, in fact a buffer, which insulates the housing 260 from impact loads when the housing is dropped. Similar air gaps 288 are provided above the viewing window as defined in an axially extending portion 290 to provide additional protection against shock or impact loads.

As shown in FIG. 12B, an O-ring 289 is provided within the annular air gap 288. Additional shock resistance between adjoining portions of the housing 264 and the interior wall surface of the guard member include an annular rubberized shim 285.

Figure 18:
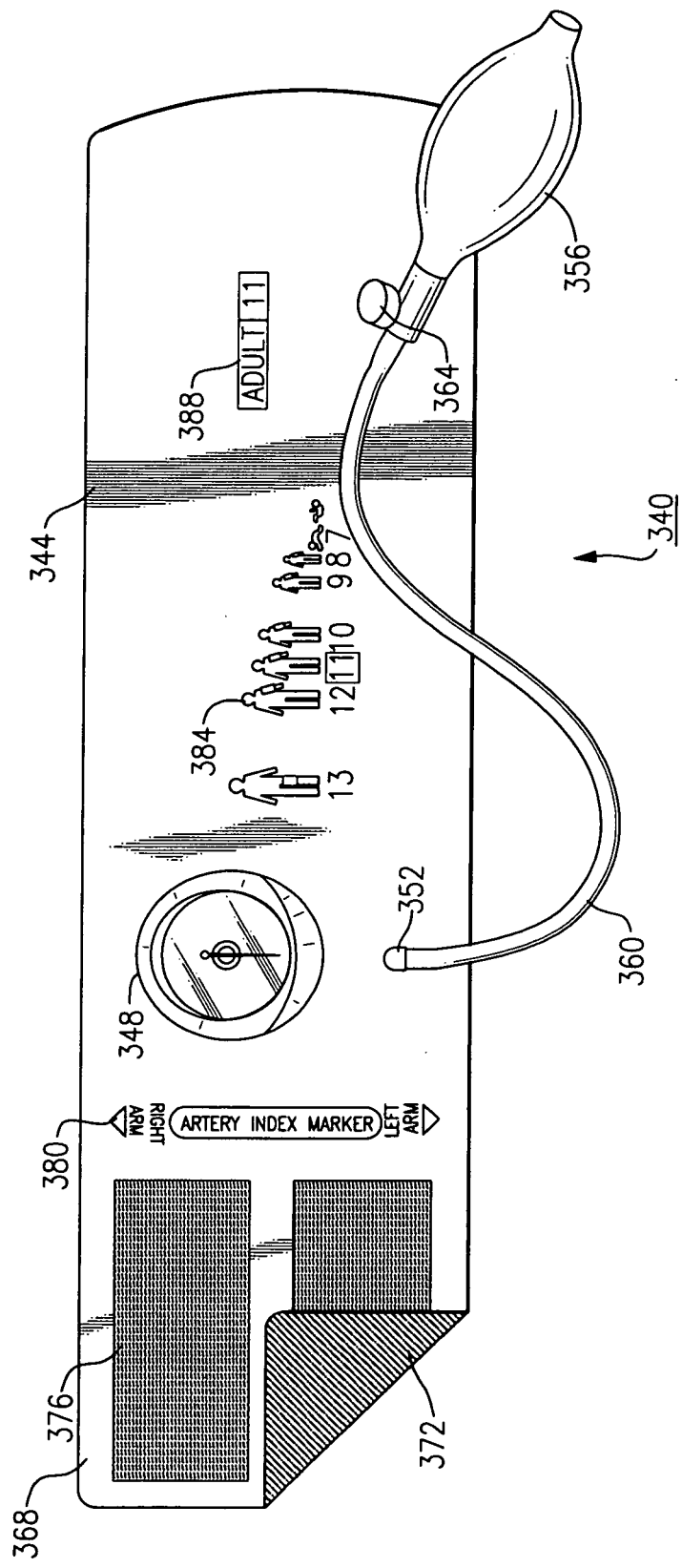
FIG. 18 is a top view of a blood pressure measuring apparatus in accordance with a preferred embodiment of the invention.
Figure 19:
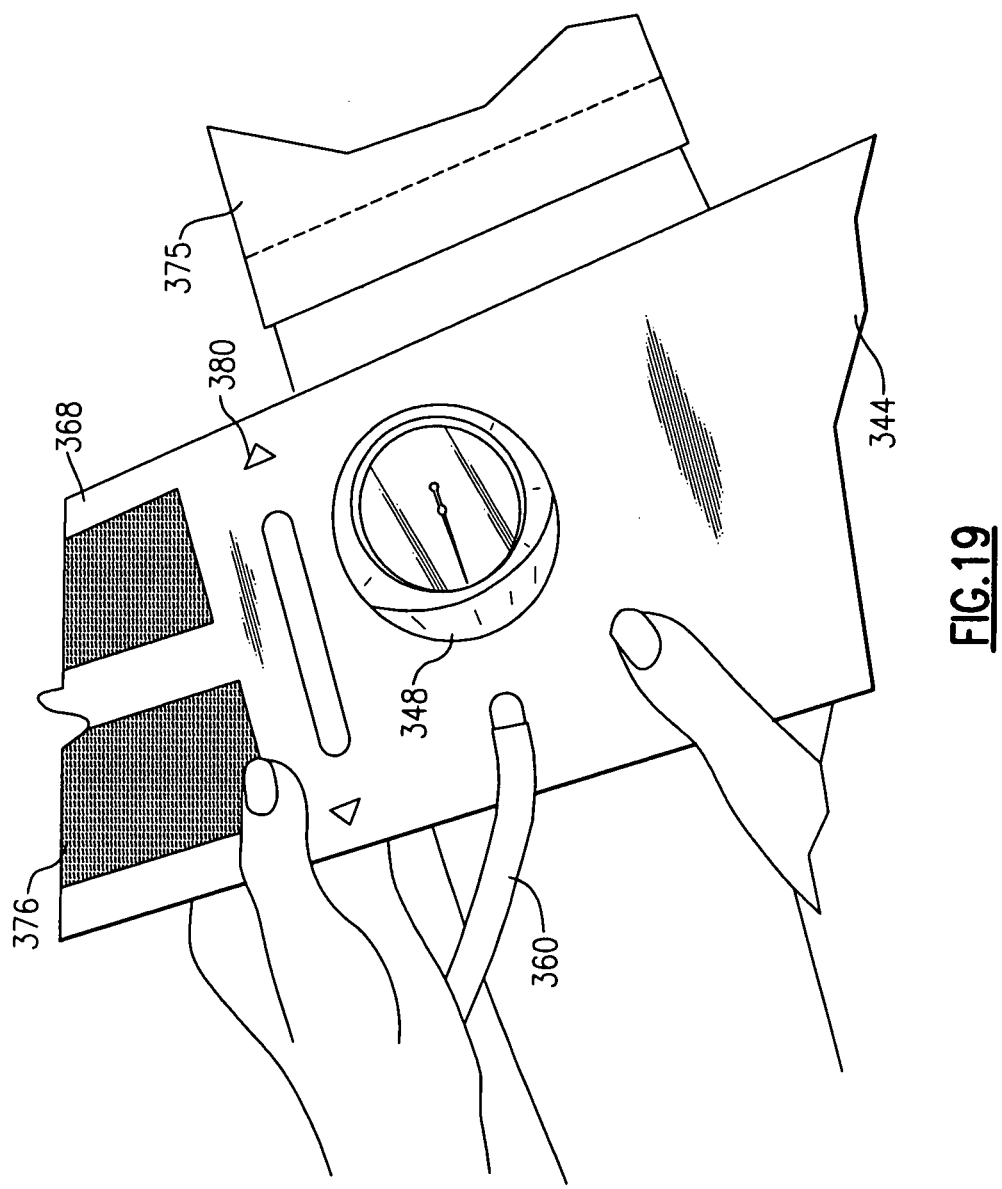
FIG. 19 is a perspective view of the inflatable sleeve of the apparatus of FIG. 18 as used with a patient.

Referring to FIGS. 18 and 19, a sleeve 344 for a blood pressure measuring apparatus 340 is herein described.

The sleeve 344 itself is constructed from a pair of sleeve portions 368, 372 made from a polyamide or other similar fluid impermeable material which are RF welded or bonded together and define an interior chamber. The interior chamber of the sleeve 344 is inflated by means of a pneumatic bulb 356 which is tethered by tubing 360 to a barb or port 352 provided on a sleeve portion 368, the barb having an opening which is in communication with the interior chamber of the sleeve. A check valve 364 provided adjacent to the pneumatic bulb 356 permits depressurization of the interior chamber of the sleeve 344 when the valve is opened.

The sleeve 344 includes hook and loop fastener portions (only one of which 376 being shown) on the outward facing sides of each of the sleeve portions 368, 372 at opposite ends of the sleeve, thereby permitting the sleeve to be formed into a cylindrical shape and secured when wrapped about the limb of a patient 375, as shown in FIG. 19. Each hook and loop fastener portion 376 is also preferably RF welded to a sleeve portion 368, 372. Specific features relating to the above noted features, including the manufacture of the herein described sleeve 344, are described in U.S. Pat. No. 6,036,718, herein previously incorporated by reference in its entirety.

When properly attached, the facing side of the sleeve portion 372 contacts the patient with the facing side of the sleeve portion 368 being exposed. According to the present embodiment, each facing side has a different color to assist in attaching same to the patient. According to the present embodiment, the sleeve 344 is two-toned with the facing side of the sleeve portion 372 having a black colored finish and the facing side of the exposed sleeve portion 368 having a lighter colored finish.

A socket or port (not shown) similar to those described above and shown for example in FIGS. 9 and 12 is also provided in the sleeve portion 368, the socket being sized for receiving a gage housing 348 which is releasably snap-fitted in the manner previously described and defined. The gage housing 348, when attached, can be rotated about its vertical axis, permitting easy visual access to either the care giver and/or the patient.

The gage housing 348 according to this embodiment is identical to that previously shown and described in FIG. 9, the housing containing a bellows assembly as well as a gearless movement mechanism which operates in the manner described above to permit circumferential movement of an indicating member relative to a dial face when pressure changes within the interior chamber of the sleeve 344 cause movement to a movable surface of the bellows assembly. The gage housing 348 also preferably includes the shock/impact resistant features previously described.

An artery index marker 380 is provided adjacent the hook and loop fastener portion 376 on the facing side of the sleeve portion 368. This marker 380 is used to align the sleeve with the brachial artery of the patient, the marker further including left and right limb indicators which are provided on respective lateral sides of the sleeve 344. When the sleeve 344 is wrapped over the arm of the patient 375, the marker is used to properly and circumferentially align the arm and the artery with the limb indicator pointing directly at the artery. The rotatability of the gage housing 348 within the sleeve 344 permits the sleeve having the attached gage housing to be used when attached regardless of orientation.

According to the present invention, sets of indicia 384, 388 are also provided on the facing side of the sleeve portion 368 designating the size of sleeve being used; that is, whether the sleeve is an adult, child or neonatal cuff. An adult sleeve is shown in the present embodiment. The gage housing 348 can be releasably attached in the manner described herein to any of the above noted sleeves, regardless of size. Moreover, the above sleeve can be used with any of the above described gage housings, including the electronic modules described in FIGS. 20-23.

FIGS. 29-35 depict additional exemplary embodiments of the present invention in which systems, methods and kits are provided for interchangeably enabling blood pressure measurements to be performed on a patient through use of different manual or electronic blood pressure measurement equipment or devices, while allowing the same cuff/sleeve to be continually worn by the patient. Because a patient can wear the same cuff/sleeve while blood pressure measurements are performed using a wide variety of blood pressure measurement equipment, the present need to frequently detach a cuff/sleeve from a patient and then locate and reattach a new sleeve/cuff is beneficially obviated.

Referring initially to FIG. 29, a cuff 1000 having an exterior surface 1010 is shown with an attached first adapter 1100. Though only partially shown in FIG. 29, the cuff 1000 can be similar or identical to any of the various cuffs/sleeves 226, 324 shown in FIGS. 9, 12, 16 and 17 in that the cuff 1000 is defined by an interior chamber (see, e.g., reference numeral 328 in FIG. 17). The interior chamber of the cuff 1000 can be formed in various manners in accordance with the present invention. By way of non-limiting example, and as shown in FIG. 17, two connected sleeves or sleeve portions 368, 372 can be connected together such that an interior chamber is defined between the two sleeves or sleeve portions. Alternatively, the cuff 1000 can be formed of a single sleeve or sleeve portion, e.g., by connecting a first edge of the sleeve to a second end of the sleeve such that an interior chamber is defined between the connected edges.

The cuff 1000 can be designed to be used only on that patient (i.e., a disposable cuff) or to be reused on multiple patients (i.e., a durable cuff). Also, the cuff 1000 can be made any suitable patient size, including but not limited to pediatric and adult sizes useful for attachment to either the arm or the thigh of a patient, wherein such size generally is indicated by textual, pictorial, color, textual and/or pictorial indicia on the cuff, e.g., as shown in FIG. 18, wherein such indicia is exemplarily identified by reference numerals 384, 388. Other representative such indicia 1050 is shown on the exterior surface 1010 of the cuff 1000 FIGS. 33 and 34, though it should be apparent that other variations and modifications are possible as well.

Figure 33:
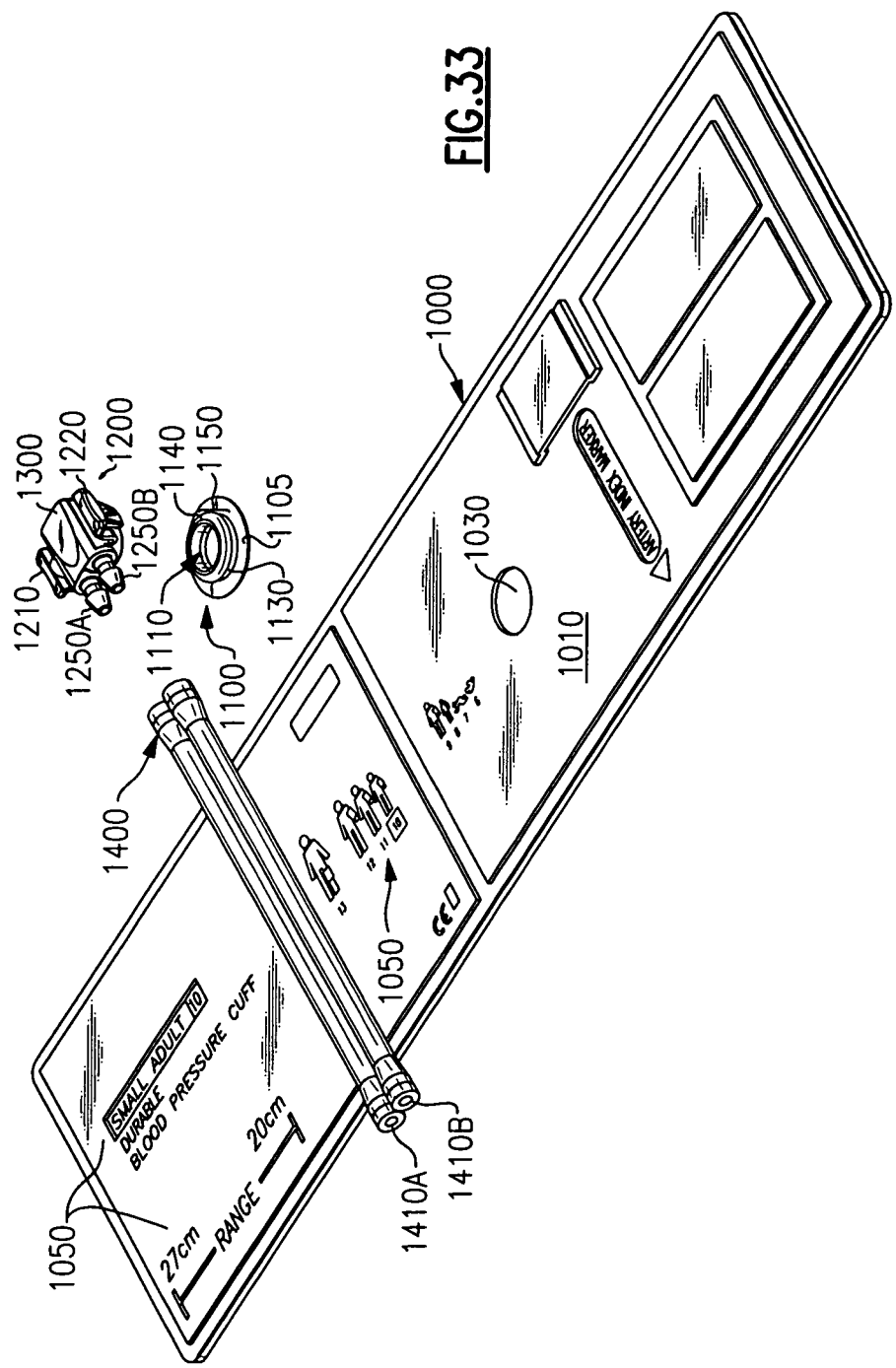
FIG. 33 is an exploded view of the components of a blood pressure measurement system in accordance with an exemplary embodiment of the present invention.

As shown in FIGS. 29 and 33, the first adapter 1100 is connected to the cuff 1000. The first adapter 1100, as described in greater detail below, includes a main body 1105 having an opening 1110 defined therewithin to provide direct fluid communication between the exterior surface 1010 and the interior chamber of the cuff 1000. The cuff 1000 has an opening 1030 (see, e.g., FIG. 33) defined therewithin, wherein the opening is sized to accommodate the first adapter 1100 and provides direct fluid communication to the interior chamber of the cuff. Generally, the first adapter 1100 is substantially irreversibly connected to the cuff 1000 at the opening 1030, e.g., by welding (e.g., RF welding, ultrasonic welding), bonding or sealing, although such connection can also be reversible as well without departing from the intended ambit of the present invention.

In accordance with an exemplary embodiment of the present invention, the first adapter 1100 can be a socket, which is disposed substantially within the exterior surface 1010 of the cuff 1000, or, as depicted in FIGS. 29 and 33, a fitting, at least a portion of which protrudes from the exterior surface of the cuff by a predetermined distance.

In either instance, the main body 1105 of the first adapter 1100 optionally can include a circumferential radial seal 1120 that is in communication with the exterior surface 1010 of the cuff 1000, wherein the radial seal, if present, has a diameter greater or smaller than the diameter of the first adapter opening depending on specific attachment conditions. Also, the first adapter 1100 can include a circumferential ring 1130 a ridge 1140. When present, the ring 1130 and ridge 1140 collectively form a portion 1150 of the first adapter 1100 that interfaces with the second adapter 1200, wherein the ring extends from the main body 1105 and the ridge extends from the ridge, as best shown in FIGS. 30C and 32-34. The main body 1105 of the first adapter 1100 can be made from the same material as the interfacing portion 1150 of the first adapter, or, alternatively, can be made of one or more different materials. Optionally, the main body 1105 of the first adapter 1100 can include a flange (not shown) that extends beneath the main body to enable or facilitate connection of the first adapter to the interior chamber of the cuff 1000.

The entire first adapter 1100 can be made of a single material, or, if instead desired, of more than one material. By way of non-limiting example, the entire first adapter 1100 can be made of a flexible plastic material or of a comparatively more rigid plastic material, wherein the specific material choice can depend on various factors such as cost, durability and/or marketplace demands. Alternatively, the first adapter 1100 can be made of two or more different materials, such as a first, flexible material and a second, comparatively more rigid (i.e., less flexible) material. In accordance with an exemplary such alternative embodiment, a portion of, or, as is currently preferred, the entirety of the main body 1105 (including, if present, the downwardly extending flange) of the first adapter 1100 can be made of a flexible plastic material, whereas one or more portions of the interfacing portion 1150 of the first adapter (i.e., the ring 1130 and/or the ridge 1140) can be made of one or more comparatively more rigid (i.e., less flexible) plastic materials. Exemplary flexible plastic materials from which the main body 1105 can be made include, but are not limited to, thermoplastic polyurethane elastomeric materials such as pellethane, polyvinyl chloride and thermal plastic rubbers, and exemplary less flexible materials from which the comparatively more rigid ring 1130 and/or ridge 1140 can be made include, but are not limited to, polycarbonate materials, acrylic materials, rigid vinyls and acrylonitrile butadiene styrene, or other rigid thermal plastics compatible for bonding with the selected flexible plastic material.

This alternative design for the first adapter 1100 is advantageous in that it provides the first adapter with dual flexibility—that is, the main body 1105 of the first adapter is flexible so as to facilitate connection of the first adapter to the cuff 1000, whereas one or more of the other portions (e.g., one or more of the ring 1130 and/or the ridge 1140) of the first adapter are comparatively more rigid (i.e., less flexible) so as to reliably maintain the connection (described below) between the first adapter 1100 and the second adapter 1200. As such, this alternative design enables the first adapter 1100 to fulfill its intended role—in the interchangeable blood pressure measurement systems, methods and kits described herein—with increased reliability and for a comparatively longer duration than if the first adapter was to be formed solely of a single material. In one variation, for example, the main body is made from a first predetermined material, the ring is made from a second predetermined material, and the ridge is made from a third predetermined material wherein all three materials are different from each other.

The system of the present invention further includes a second adapter 1200, described in greater detail below, which is releasably connected to the first adapter 1100, and which can have various designs as shown, e.g., in the first exemplary embodiment of FIGS. 30A and 30B and the second exemplary embodiment of FIGS. 31A and 31B. By way of non-limiting example, the first and second adapters 1100, 1200 are reversibly (e.g., releasably connected), such as, by being threaded together, by being friction fitted, through detent action or, as illustrated in FIG. 32, via snap fitting. To enable or facilitate the snap fitting connection between the first adapter 1100 and the second adapter 1200, and again as shown in FIG. 32, the first adapter can include a circumferential ridge 1140 beneath which first and second connection members 1210, 1220 of the second adapter can snap fit. By virtue of the design of the first and second adapters and further due to the snap fitting connection therebetween, the second adapter 1200 generally is at least partially, substantially, or entirely (i.e., 360°) rotatable while it is connected to the first adapter 1100.

Techniques for achieving the releasable connection between the first adapter 1100 and the second adapter 1200 include, but are not limited to, providing the second adapter with recesses within which fingers or other protruding portions of the first adapter can fit (e.g., via snap fitting or detent), or by providing the second adapter with a plunger-like mechanism to expand inwardly or outwardly following a predetermined action (e.g., upon the pressing of a button or upon activation of a trigger) in order to hold or release the first adapter in/from tactile communication with the second adapter.

Alternatively, the first adapter 1100 can be adapted to include an elastomeric lip in lieu of the radial seal 1120, in which case the second adapter can include a flanged portion to fit over the elastomeric lip. This alternative embodiment also will allow for the second adapter 1200 to be at least partially, substantially, or entirely (i.e., 360°) rotatable while it is connected to the first adapter 1100 and may be more resistant to plastic deformation than the snap fitting and may also further deter the formation of unwanted dirt and debris between the first adapter 100 and the second adapter 1200.

In order to further reduce the accumulation of unwanted foreign matter and materials such as dust, dirt or debris (collectively referred to herein as "contaminants"), at least one screening/filtering component can be disposed within the second adapter 1200 at a predetermined position located within the path of air. In accordance with an exemplary embodiment, and as shown in FIGS. 31B and 32, a plurality of screening components 1280 can be disposed within one, or, as is currently preferred, both of a first chamber 1270A and a second chamber 1270B of the second adapter 1200. As best shown in FIG. 30B, one or more screening components 1280 also can be included within the single chamber 1260 of the embodiment of the second adapter 1200 shown in FIGS. 30A and 30B. In each instance, the presence of the one or more screening components 1280 beneficially prevents, or at least substantially reduces the possibility of contaminants that may be present within the cuff 1000 from entering, let alone traveling through the second adapter 1200.

The one or more screening components 1280 can have the same shape and dimensions, or can have varied dimensions and/or shape (e.g., varied height and/or width). However, as shown in FIG. 32, each screening component 1280 generally is a substantially cylindrically shaped member. This is generally the case whether the screening component(s) 1280 are present in a second adapter 1200 of the type shown in FIGS. 30A and 30B or a second adapter of the type depicted in FIGS. 31A and 31B. The one or more screening components 1280 can be connected or attached to their placement locations within the second adapter 1200 via a variety of known attachment techniques, e.g., by being molded directly into the second adapter and/or through the use of an adhesive.

The exact number of screening components 1280 present within the second adapter 1200 can vary; however, there should be enough such that the second adapter remains readily air permeable, yet also such that contaminants are reliably collected therein. In an embodiment wherein a plurality of screening components 1280 are located within both the first and second chambers 1270A, 1270B of a second adapter 1200 of the type shown in FIGS. 31A and 31B, the number in each chamber can vary as well, e.g., based on the size and/or shape of the screening components, the dimensions of the chambers, etc. However, according to an exemplary embodiment of the present invention, the same numbers of screening components are disposed within each of the first chamber 1270A and the second chamber 1270B. Generally, the number of screening components 1280 within each chamber 1270A, 1270B can range from five to fifteen.

Figure 30A:
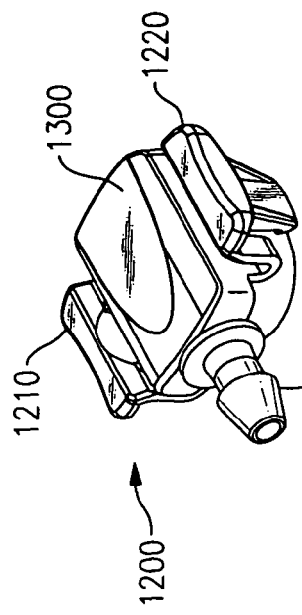
FIGS. 30A and 30B are perspective and bottom views of a first exemplary embodiment of a second adapter in accordance with the present invention.
Figure 30C:
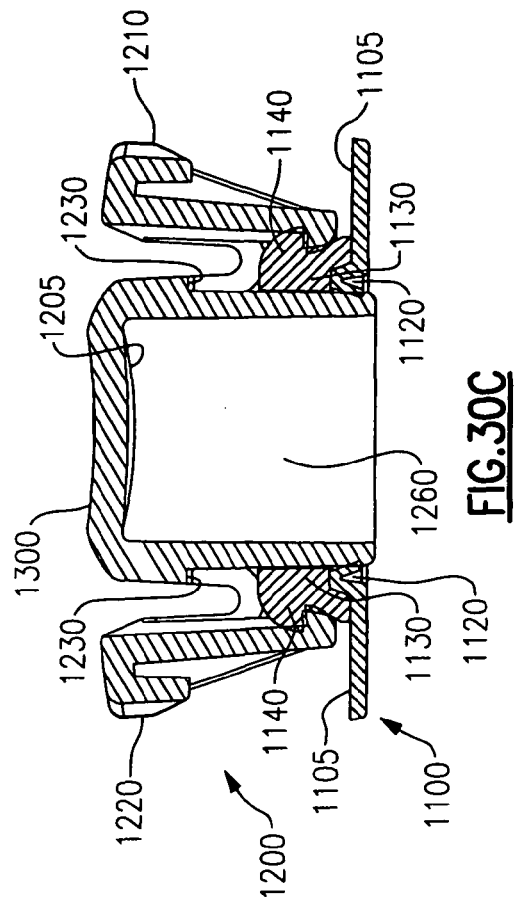
FIG. 30C is a front view, with cut away of a first adapter releasably connected to the second adapter of FIGS. 30A and 30B FIGS. 31A and 31B are perspective and bottom views of a second exemplary embodiment of a second adapter in accordance with the present invention.
Figure 30B:
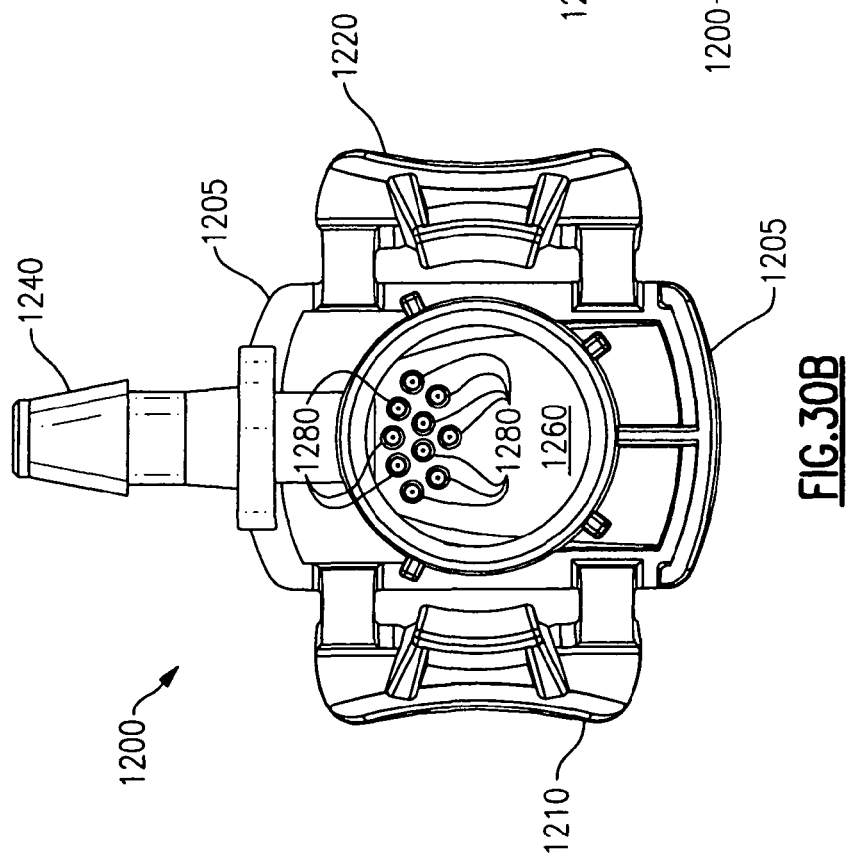

A total of ten screening components 1280 are present within the single chamber 1260 in FIG. 30B. However, the total number of screening components in the single chamber 1260 of a second adapter 1200 of the type shown in FIGS. 30A and 30B can vary above or below ten, e.g., based on the size and/or shape of the screening components, the dimensions of the single chamber, etc.

The screening component(s) 1280 should be made from at least one material that reliably collects contaminants, yet that does not otherwise inhibit the passage of air through the second adapter 1200 so as not to deter or prevent the functioning of a blood pressure measurement system within which the second adapter is incorporated. To that end, and by way of non-limiting example, the screening component(s) 1280 can be formed of a mesh material (e.g., wire screen, a cloth material, or a plastic material) or a membrane (e.g., a membrane of a sintered material, a fibrous material or a fabric). Each of the one or more screening components 1280 can be made from the same or from a different material.

By virtue of being made of a mesh or membrane, the one or more screening components 1280 are at least partially self-cleaning, wherein such cleaning occurs by reverse direction air flow from the first adapter 1100 into the second adapter 1200. Alternatively, any or all of the one or more screening components 1280 can be cleaned or replaced on a periodic or scheduled basis, wherein access to the screening components is gained by disconnecting, detaching or otherwise separating the second adapter 1200 from the blood pressure measurement system and then opening the second adapter.

It should be noted that although FIGS. 30B, 31B and 32 depict the one or more screening components 1280 as being part of the second adapter 1200, it is also possible for one or more screening components to be located elsewhere within the blood pressure measurement system (e.g., within or as part of the first adapter 1100) in lieu of or in addition to the one or more screening components that are included within the second adapter. Moreover, the specific location of the one or more screening components 1280 within the second adapter 1200 could be changed from the depicted locations, if desired, without undue experimentation.

As depicted in FIGS. 30A, 31A, 32 and 33, and in accordance with an optional embodiment of the present invention, a covering element or member 1300 can be releasably connected to a top opening of the main body 1205 of the second adapter 1200. Such connection can be made, by way of non-limiting example, by snap fitting first and second connection members 1310, 1320 of the covering element 1300 under a circumferentially protruding ridge 1230 of the second adapter (see FIG. 32). If present, the covering member 1300 generally serves only an aesthetic purpose and, to that end, can bear of textual and/or pictorial indicia, e.g., indicia relating to the manufacturer of the equipment utilized in connection with the system.

Referring now to FIGS. 30A and 30B, an exemplary embodiment of the second adapter 1200 of the present invention is illustrated in detail. The second adapter 1200 of FIGS. 30A and 30B includes a main body 1205, as well as a single barb 1240 that protrudes from the main body. As shown in FIG. 30B, a single chamber 1260 defined within the interior of the main body 1205 of the second adapter 1200 is in direct fluid communication with interior of the barb 1240. Therefore and once the first adapter 1100 has been connected to the second adapter 1200 as shown in FIG. 30C, the single chamber 1260 is in direct fluid communication with the opening 1110 of the first adapter. And because the opening 1100 defined within the main body 1105 of the first adapter 1100 is in direct communication with the interior chamber of the cuff 1000, the second adapter 1200 is in communication with the interior chamber of the cuff. A section of hose or tubing can be connected to the barb 1240, as will be described in greater detail below, to interchangeably provide fluid communication between the interior chamber of the cuff 1000 and a number of different blood pressure measurement devices.

Another exemplary embodiment of the second adapter 1200 is illustrated in FIGS. 31A and 31B. The size, structure and components of the second adapter 1200 of FIGS. 31A and 31B are generally identical to those of the second adapter depicted in FIGS. 30A and 30B. Two barbs 1250A, 1250B protrude from the main body 1205 of the second adapter depicted in FIGS. 31A and 31B, as opposed to the single barb design of the second adapter of FIGS. 30A and 30B. The barbs 1250A, 1250B extend from one side of the main body 1205 of the second adapter 1200 and are identical according to this embodiment. The barbs 1250A, 1250B are spaced apart from one another to permit hosing to be attached, as described below. Also, whereas the FIGS. 30A and 30B second adapter 1200 includes only a single chamber 1260 in direct contact with its barb 1240, the FIGS. 31A and 31B second adapter includes a first chamber 1270A, a second chamber 1270B and a dividing zone 1270C defined therebetween. Both the first and second chambers 1270A 1270B are in communication with the opening 1110 of the first adapter 1100 once the first adapter has been connected to the second adapter 120 of FIGS. 31A and 31B, however, the first chamber 1270A is in direct fluid communication with the first barb 1250A, but not the second barb 1250B, and the second chamber 1270B is in direct fluid communication with the second barb 1250B but not the first barb 1250A.

In accordance with the FIGS. 31A and 31B embodiment of the second adapter 1200, and once the first adapter 1100 has been connected to the second adapter, the first and second chambers 1270A, 1270B are in direct fluid communication with the opening 1110 of the first adapter. And because the opening 1100 defined within the main body 1105 of the first adapter 1100 is in direct communication with the interior chamber of the cuff 1000, the second adapter 1200 is in communication with the interior chamber of the cuff. A quantity of hose or tubing having a female end also can be attached or connected to the barbs 1250A, 1250B of the FIGS. 31A and 31B second adapter 1200, as will be described in greater detail below, to provide fluid communication between the cuff 1000 and a blood pressure measurement device.

It is understood that the FIGS. 30A and 30B embodiment of the second adapter 1200 can be adapted to include one recess in lieu of one barb 1240 and the FIGS. 31A and 31B embodiment of the second adapter can be adapted to include two recesses in lieu of the two barbs 1240A, 1240B or to replace one of the barbs with a recess, wherein the presence of the recess(es) will allow for attachment or connection of a quantity of hose or tubing having a male end.

Figure 34:
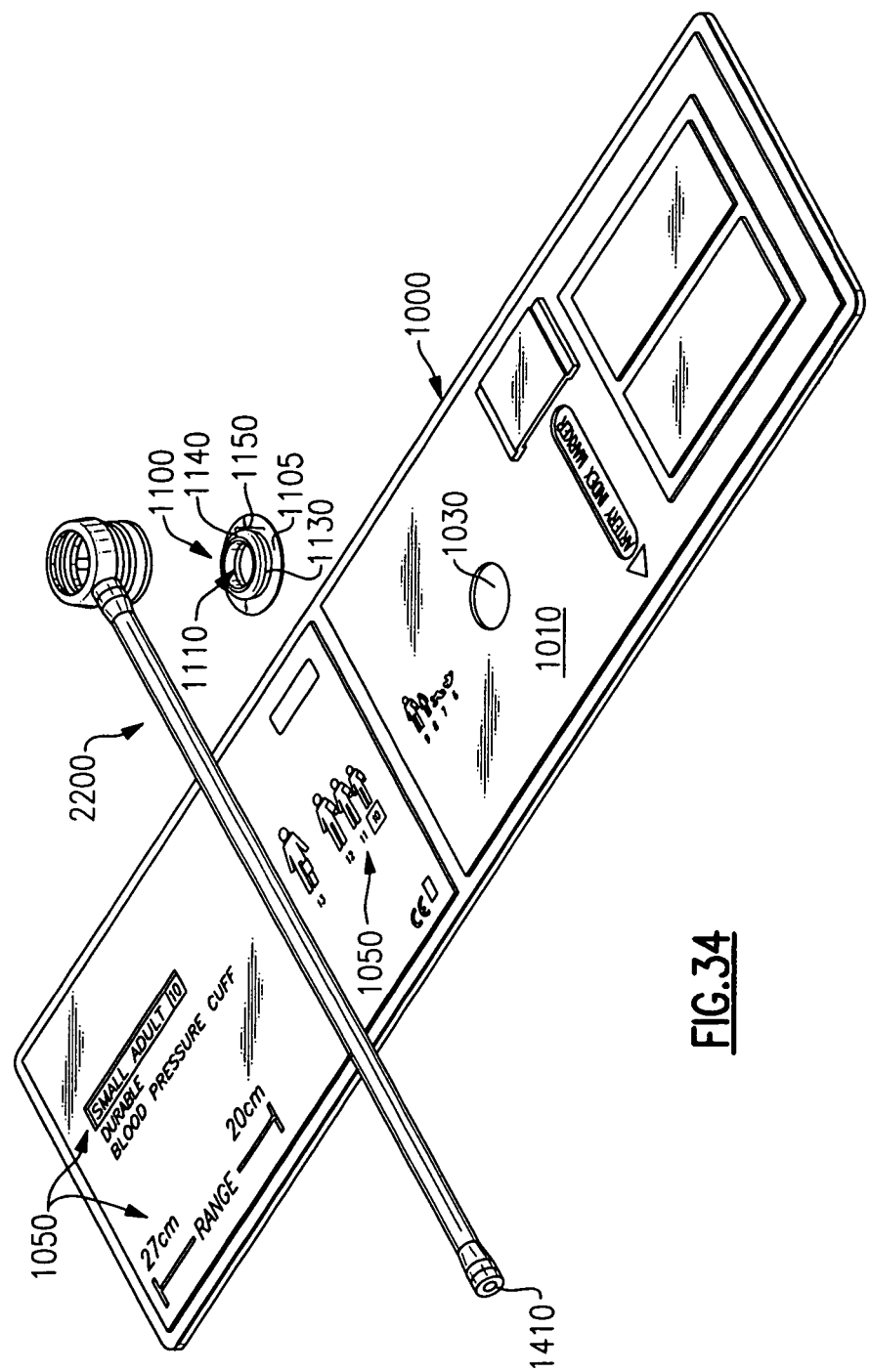
FIG. 34 is an exploded view of the components of a blood pressure measurement system in accordance with an alternative exemplary embodiment of the present invention.
Figure 35:
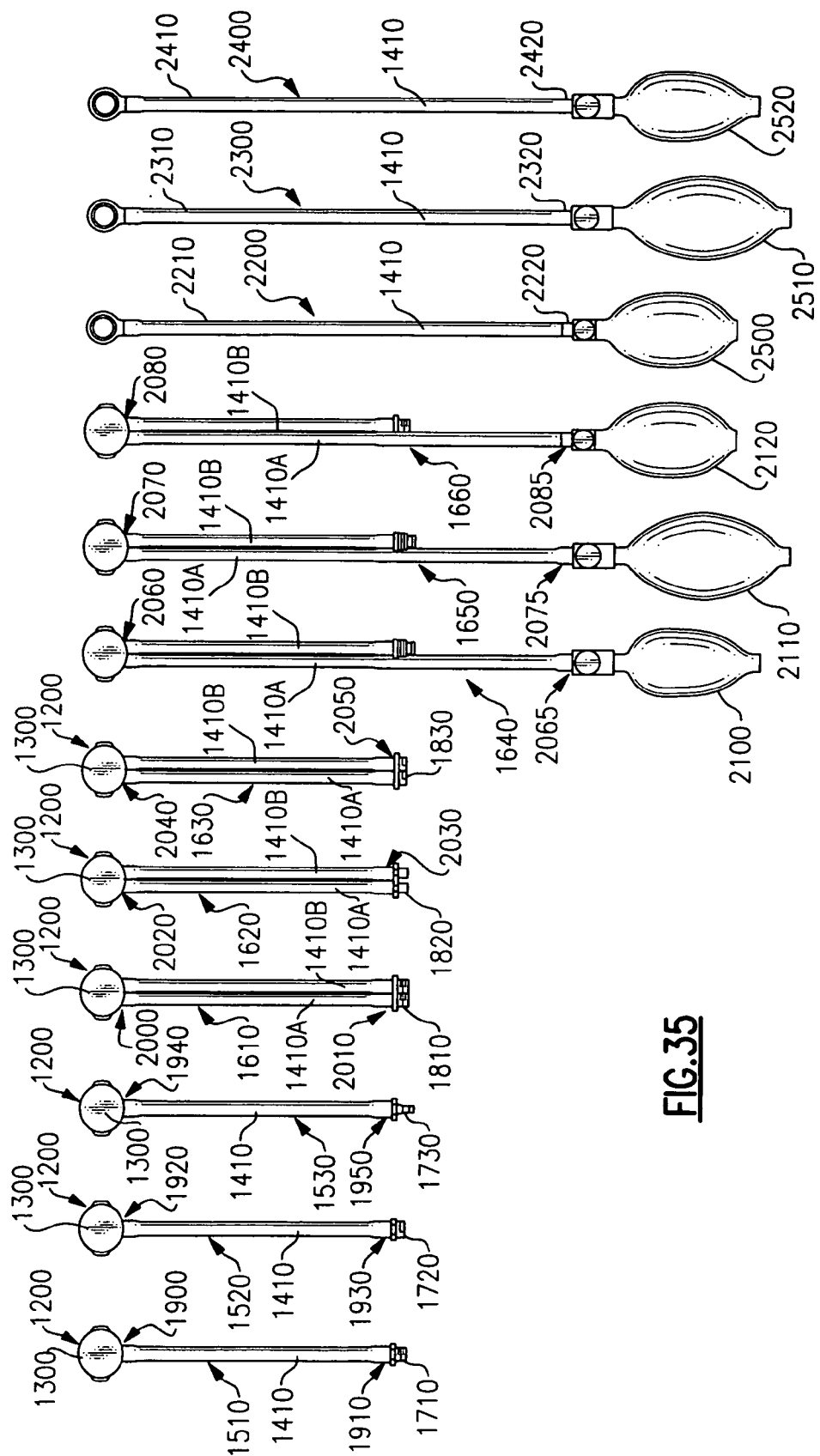
FIG. 35 is a top view of various exemplary configurations of an attached hose in accordance with the present invention.

As shown in FIGS. 33-35, the presence of the second adapter 1200 enables interchangeable, individual connection between the cuff (via the first adapter) and any of a plurality of blood pressure measuring devices. Such connection generally will be completed occur by attaching an end of at least one hose to the protruding barb 1240 of the second adapter of FIGS. 30A and 30B or to the protruding barbs 1250A, 1250B of the second adapter 1200 of FIGS. 31A and 30B. In other words, if, as shown in FIG. 33, the hose 1400 to be attached is defined by a two lumen 1410A, 1420A configuration, then a second adapter 1200 having two barbs 1250A, 1250B of the type shown in FIGS. 31A and 31B is utilized. If, instead, the hose 1400 has only a single lumen 1410 configuration, as depicted in FIG. 34, then a second adapter 1200 having one barb 1240 of the type shown in FIGS. 30A and 30B would be utilized.

The present invention is highly advantageous in that it allows for switching between single lumen 1410 and multiple lumen (e.g., dual lumen 1410A, 1410B) hose attachments 1400 without necessitating removal of the cuff 1000, and with a minimum of added effort. For example, a second adapter 1200 having one barb 1240, as shown in FIGS. 30A and 30B, may be connected to the first adapter 1100 if a patient's blood pressure is to be measured by a blood pressure measurement device that requires communication with a cuff 1000 via a hose 1400 having only one lumen 1410. If, earlier or subsequently, the patient's blood pressure must be measured by a blood pressure measurement device that requires communication with a cuff 1000 via a hose 1400 having two lumens 1410A, 1410B, then a second adapter 1200 having two barbs 1250A, 1250B, as shown in FIGS. 31A and 31B, may be connected to the first adapter 1100. Therefore, in accordance with the present invention, rather than requiring replacement of the entire cuff 1000 in order to allow for blood pressure measurements to be performed through use of different equipment/devices that require communication with the cuff via different hose attachments having different numbers of lumens, all that is necessary, at most, is to replace the attached hose 1400 and/or the second adapter 1200.

The preceding interchangeability feature is highly beneficial because it is not uncommon for the same patient to require his or her blood pressure to be measured by several different blood pressure measurement equipment or devices, wherein at least some of those devices require hose attachments having a different number of lumens to be connected thereto. Similarly, this interchangeability also is applicable to situations in which multiple patients, each of which is wearing a cuff that might be of a different size and/or type than as the other, seek to have blood pressure measurements performed by one or more piece of blood pressure measurement equipment. To these ends, exemplary FIG. 35 illustrates three exemplary, removable single lumen hose attachments 1510, 1520, 1530 and three exemplary, removable dual lumen hose attachments 1610, 1620, 1630, wherein each of the six hose attachments is capable of being individually, releasably connected to one or more different electronic blood pressure measurement devices (not shown). Generally, and as shown in FIG. 35, each of the hose attachments 1510-1530, 1610-1630 is attached to an electronic blood pressure measurement device through use of a connector, wherein the specific choice of connector will depend on the type and/or manufacturer of the blood pressure measurement device. For the single lumen hose attachments 1510-1530, exemplary connectors include, but are not limited to, a screw/luer type connector 1710, a locking type connector 1720, a bayonet type connector 1730, and a barb type connector (not shown). For dual lumen hose attachments 1610-1630, exemplary connectors include, but are not limited to, a screw/luer type connector 1810, a luer lock type connector 1820, a locking type connector 1830, and a barb type connector (not shown).

By way of non-limiting example, the single lumen hose attachment 1510 shown in FIG. 35 can be connected at its first end 1900 to the barb 1240 of the second adapter 1200 shown in FIGS. 30A and 30B and can be fitted with a screw type connector 1710 to individually connect the second end 1910 of the hose attachment 1510 to blood pressure measurement devices such as a Welch Allyn Spot vital signs device, or a Welch Allyn VSM Series device, or a Welch Allyn Atlas Monitor, each of which is commercially available from Welch Allyn, Inc. of Skaneateles Falls, N.Y. USA. Also by way of non-limiting example, the single lumen hose attachment 1520 shown in FIG. 35 can be connected at its first end 1920 to the barb 1240 of the second adapter 1200 shown in FIGS. 30A and 30B and can be fitted with a locking type connector 1620 to individually connect the second end 1930 of the hose attachment 1520 to blood pressure measurement devices such as the Propaq vital signs monitor commercially manufactured by Welch Allyn Protocol, Inc. of Beaverton, Oreg. USA. Still, also by way of non-limiting example, the single lumen hose attachment 1530 shown in FIG. 35 can be connected at its first end 1940 to the barb 1240 of the second adapter 1200 shown in FIGS. 30A and 30B and can be fitted with a bayonet type connector 1730 to individually connect the second end 1950 of the hose attachment 1530 to blood pressure measurement devices commercially available from Agilent Technologies of Palo Alto, Calif. USA, by Spacelabs of Redmond, Wash. USA, by Datascope of Montvale, N.J. USA, Siemens AG of Munich, GERMANY, and by Criticare Systems, Inc. of Waukesha, Wis. USA. By way of still further non-limiting example, the dual lumen hose attachment 1610 shown in FIG. 35 can be connected at its first end 2000 to the barbs 1250A, 1250B of the second adapter 1200 shown in FIGS. 31A and 31B and can be fitted with a screw type connector 1810 to individually connect the second end 2010 of the hose attachment 1610 to blood pressure measurement devices such as a Welch Allyn Spot Ultra vital signs device, which is commercially available from Welch Allyn of Skaneateles Falls, N.Y. USA, or to a Critikon Dynamap Monitor, which is commercially available from DRE Medical Incorporated of Louisville, Ky. USA. By way of yet still further example, the dual lumen hose attachment 1620 shown in FIG. 35 can be connected at its first end 2020 to the barbs 1250A, 1250B of the second adapter 1200 shown in FIGS. 31A and 31B and can be fitted with a luer lock type connector 1820 to individually connect the second end 2030 of the hose attachment 1620 to blood pressure measurement devices commercially available from Datascope of Montvale, N.J. USA and Colin Medical Instruments Corp of San Antonio, Tex. USA. By way of yet still even further non-limiting example, the dual lumen hose attachment 1630 shown in FIG. 35 can be connected at its first end 2040 to the barbs 1250A, 1250B of the second adapter shown in FIGS. 31A and 31B and can be fitted with a locking type connector 1830 to individually connect the second end 2050 of the hose attachment 1630 to blood pressure measurement devices such as GE Marquette monitors, which are commercially available from GE Healthcare of Waukesha, Wis. USA.

FIG. 35 further shows three (3) additional dual lumen hose attachments 1640, 1650, 1660 that can be individually, releasably connected to one or more manual blood pressure measurement devices. For example, the hose attachment 1640 is defined by a first end 2060 and an opposing second end 2065, the firmer including first and second lumens 1410A, 1410B. The first end 2060 of the hose attachment 1640 is connected to the second adapter 1200 shown in FIGS. 31A and 31B. The second end 2065 of the first lumen 1410A is adapted for connection to a hand-held pneumatic bulb 2100, whereas the second end of the second lumen 1410B is adapted for connection, e.g., via a luer lock connector, to a gauge (e.g., a hand gauge). By way of non-limiting example, the hose attachment 1640 can be individually connected to the classic pocket, SRC pocket and wall model manual blood pressure measurement devices, commercially available from Welch Allyn, Inc. of Skaneateles Falls, N.Y. USA. The hose attachment 1650 is identical to the hose attachment 1640, except that the second end 2070 of the first lumen 1410A of the hose attachment 1650 is designed to be connected to a larger bulb 2110 than the second end 2065 of the first lumen 1410A of hose attachment 1640. The hose attachment 1650 can be individually connected to at least the same manual blood pressure measurement devices at hose attachment 1640. Hose attachment 1660 also has a first end 2080 and a second end 2085 and includes first and second lumens 1410A, 1410B. The first end 2080 of the hose attachment 1660 is connected to the second adapter 1200 shown in FIGS. 31A and 31B. The second end 2085 of the first lumen 1410A is adapted for connection to a disposable hand pneumatic bulb 2120, whereas the second end of the second lumen 1410B is adapted for connection, via a screw connector 1850, to a gauge (e.g., a hand gauge). By way of non-limiting example, the hose attachment 1630 can be individually connected to various disposable inflation systems commercially available from Welch Allyn, Inc. of Skaneateles Falls, N.Y. USA.

FIG. 35 further depicts three additional embodiments 2200, 2300, 2400 of a single lumen system wherein the hose portions 2210, 2310, 2410 can be either releasably or non-releasably attached to an adapter 2400, which is releasably connectable to the first adapter 1100 as shown in FIG. 34. Each of the systems 2200, 2300, 2400 is similar in its design and function and are described in more detail in U.S. Pat. Nos. 6,796,186, 6,746,406, 6,615,666, 6,578,428, 6,481,291, 6,422,086, each of which is incorporated by reference in its entirety herein.

During use of system 2200, the second end 2220 of the hose portion 2210 is connected to a small sized, manually operated pneumatic bulb 2500. The system 2200 can be utilized, by way of non-limiting example, in connection with the DS44 series of blood pressure measurement devices commercially available from Welch Allyn, Inc. of Skaneateles, N.Y. USA. During use of system 2300, the second end 2320 of the hose portion 2310 is connected to a large sized bulb 2510. The system 2300 can be utilized, by way of non-limiting example, in connection with the DS45 and the SRC integrated series of blood pressure measurement devices commercially available from Welch Allyn, Inc. of Skaneateles, N.Y. USA. During use of system 2400, the second end 2420 of the hose portion 2410 is connected to a disposable bulb 2520. Like the system 2300, the system 2400 also can be utilized, by way of non-limiting example, in connection with the DS45 and the SRC integrated series of blood pressure measurement devices commercially available from Welch Allyn, Inc. of Skaneateles, N.Y. USA.

Referring once again to FIG. 29, the interchangeability of the present invention is highlighted by the depiction of three systems 2600, 2700, 2800, each of which can be interchangeably connected to the first adapter 1100 to be placed in direct fluid communication with the interior chamber of the cuff. The first system 2600 is of the type described above and depicted in FIG. 35 with reference numerals 2200, 2300 and 2400 and can be individually connected to a variety of blood pressure measurement devices, such as the DS44 series, DS45 series and/or SRC integrated series of blood pressure measurement devices commercially available from Welch Allyn, Inc. of Skaneateles, N.Y. USA. The second system 2700 includes a second adapter 1200 of the type depicted in FIGS. 30A and 30B wherein a first end of hose attachment 1400 having a single lumen 1410 has been connected to the second adapter and wherein a screw type connector 1710 has been connected to the second end of the hose attachment to enable the system 2700 to be individually connected to different blood pressure measurement equipment than the system 2600, e.g., a Welch Allyn Spot vital signs device, or a Welch Allyn VSM Series device, or a Welch Allyn Atlas monitor, each of which is commercially available from Welch Allyn, Inc. of Skaneateles Falls, N.Y. USA. The third system 2800 includes a second adapter 1200 of the type depicted in FIGS. 31A and 31B wherein a first end of hose attachment 1400 having a dual lumen 1410A, 1410B has been connected to the second adapter and wherein a screw type connector 1810 has been connected to the second end of the hose attachment to enable the system 2800 to be individually connected to different blood pressure measurement equipment than the systems 2600, 2700, e.g., a Welch Allyn Spot Ultra vital signs device, which is commercially available from Welch Allyn of Skaneateles Falls, N.Y. USA, or to a Critikon Dynamap monitor, which is commercially available from DRE Medical Incorporated of Louisville, Ky. USA.

Thus, the system defined by the present invention is highly versatile and efficient in that it enables the same inflatable cuff 100 to remain connected to a patient while blood pressure measurements can be made by different blood pressure measurement equipment from one or more manufacturers regardless of the differences (e.g., manual versus electronic, single lumen hose attachment(s)versus dual lumen hose attachment(s), screw connector versus luer connector versus locking connector versus barb connector versus bayonet connector, etc.) among the equipment. Still additional versatility and efficiency is provided due to the system of the present invention being equally applicable to enable one or more blood pressure measurements to be taken from multiple patients, each of whom is wearing a cuff that may be of a different size and/or type than the other, via one or more pieces of blood pressure measurement equipment. These are important advantages over the current approach, which, in order to conduct different types of blood pressure measurement on one or more patients using different blood pressure measurement equipment or devices, necessitates devoting comparatively more time and manpower in order to attach an initial cuff, remove the initial cuff, then locate and attach a new cuff or to find the necessary connections to enable such measurements to occur in each instance. The benefits of the present invention will be especially pronounced in a hospital, trauma center or HMO environment, in which there is often a need to measure the blood pressure or one or more patients using different techniques and/or equipment, and where there can be significant adverse consequences due to lost time and/or overtaxed manpower.

PARTS LIST FOR FIGS. 1-35

10 blood pressure measuring device or apparatus
12 gage housing
12B gage housing
14 interior cavity
16 circumferential inner wall
18 open top end
19 reflexed portion
20 bottom end
20B bottom end
21 outer edge (support plate)
22 bubble or viewing window
24 downwardly extending portion
26 bottom opening
28 horizontal support plate
28A horizontal support plate
30 top facing side
32 bottom facing side
34 central through opening
36 sleeve
36A sleeve
36B sleeve
40 movement mechanism
42 diaphragm subassembly
44 diaphragm
44B diaphragm
45 circumferential ridge
46 O-ring
46B O-ring
47 outer edge
47B outer edge
48 pan
49 wave-like surfaces
49B wave-like surfaces
50 cavity
51 cavity
52 contact surface
53 lower end
54 axially displaceable shaft member
55 bottom end
56 tubular member
57 top end
58 top cap portion
59 end-ribbon spring
61 end-ribbon spring
62 indicating member
63 dial face
63A dial face
65 O-ring
66 threads
67 slot
68 biasing spring
68B biasing spring
69 recess
70 ribbon spring member
72 one end
73 threads 75 threads
80 shoulder
82 docking hub
114 circumferential groove
118 O-ring
140 gage or instrument housing
142 cuff
144 sleeve portion
146 sleeve portion
148 inner volume
152 upper housing portion
154 lower housing portion
156 intermediate portion
158 interior cavity
162 slot
165 support plate
166 detachable stethoscope adapter
167 dial face
170 arm
171 movement mechanism
174 extending attachment portion
176 port
178 hose
180 female connector
184 port
190 socket
194 instrument or gage housing
196 ball-shaped engagement end
198 direction
200 opening
202 peripheral bumper
2-6 ridge
210 gage housing
212 upper housing portion
214 movement mechanism
218 narrowed lower housing portion
220 engagement or mating end
222 socket
224 end opening
226 blood pressure sleeve or cuff
228 socket opening
232 rubberized peripheral guard or bumper member
234 stepped portion
236 gap
240 ribbon spring
242 axially displaceable shaft member
246 contained diaphragm
248 indicating member
250 circumferential channel
260 gage housing
264 upper housing portion
268 narrowed lower housing portion
270 engagement end
271 end opening
272 circular face groove
274 movement mechanism
276 bottom surface
280 rubberized guard member
284 radially extending portion
285 rubberized shim
286 air gap
288 air gap
289 O-ring
290 axially extending portion
292 movement mechanism
294 gage housing
296 gage housing
297 threaded end
298 inlet port
299 bottom opening
300 port
302 cap
304 opening
305 tubular member
306 gage housing
307 pneumatic bulb
308 opening
309 output end
310 inlet port
320 socket
324 sleeve
328 interior
340 blood pressure measuring apparatus
344 sleeve
348 gage housing
352 barb or port
356 pneumatic bulb
360 tubing
364 check valve
368 sleeve portion
372 sleeve portion
375 patient
376 hook and loop fastener portion
380 artery index marker
384 indicia
388 indicia
400 blood pressure measuring assembly
404 sleeve
408 port
412 opening
416 interior, sleeve
420 gage housing
424 proximal end
432 electronic movement mechanism
434 pneumatic bulb
438 hose
442 coupling
445 hook and loop fasteners
446 bleed valve
450 capacitance transducer assembly
454 capacitance pressure sensor transducer
458 oscillator circuit
462 measurement and processing circuit
466 counter circuit
470 data processor
474 reference oscillator
475 I/O devices
476 actuable button
478 display
480 metallic conductor layer
484 circuit board
488 ground conductor layer
492 side
496 metal ring
500 pins
504 ring conductor
508 support plate
512 metallic diaphragm
516 O-ring
520 snap-on cap
522 port
524 multiple snaps
530 inverter gate
534 inverter gate 538 resistor
540 capacitance transducer
542 capacitor
544 capacitor
548 low pass filter
552 inverter gate
556 resistor
560 electronic gage module
564 housing body
566 upper or major housing section
568 proximal engagement portion
572 opening, end
576 peripheral bumper
582 capacitance transducer sensor assembly
584 LCD
586 circuit board
588 viewing window
594 processor
598 button
600 batteries
640 electronic gage housing or module
644 housing body
648 valve
652 pressure-sensitive switch
656 sensor
660 port
666 processor
670 display
674 wireless link
1000 cuff
1010 exterior surface
1030 opening
1050 indicia
1100 first adapter
1105 main body
1110 opening
1120 radial seal
1130 ring
1140 ridge
1150 interfacing portion
1200 second (additional) adapter
1205 main body
1210 first connection member
1220 second connection member
1230 ridge
1240 barb
1250A barb
1250B barb
1260 single chamber
1270A first chamber
1270B second chamber
1270C channel
1280 screening component
1300 covering element
1310 first connection element
1320 second connection element
1400 hose/hose attachment
1410 single lumen
1410A first lumen
1420B second lumen
1510 single lumen hose attachment
1520 single lumen hose attachment
1530 single lumen hose attachment
1610 dual lumen hose attachment
1620 dual lumen hose attachment
1630 dual lumen hose attachment
1640 dual lumen hose attachment
1650 dual lumen hose attachment
1660 dual lumen hose attachment
1710 screw type connector
1720 locking type connector
1730 bayonet type connector
1810 screw type connector
1820 luer lock type connector
1830 locking type connector
1900 first end of hose attachment
1910 second end of hose attachment
1920 first end of hose attachment
1930 second end of hose attachment
1940 first end of hose attachment
1950 second end of hose attachment
2000 first end of hose attachment
2010 second end of hose attachment
2020 first end of hose attachment
2030 second end of hose attachment
2040 first end of hose attachment
2050 second end of hose attachment
2060 first end of hose attachment
2065 second end of hose attachment
2070 first end of hose attachment
2075 second end of hose attachment
2080 first end of hose attachment
2085 second end of hose attachment
2100 bulb
2110 bulb
2120 bulb
2200 first attached adapter and hose system
2210 hose portion
2220 second end
2300 second attached adapter and hose system
2310 hose portion
2320 second end
2400 third attached adapter and hose system
2410 hose portion
2420 second end
2500 bulb
2510 bulb
2520 bulb
2600 first exemplary system
2700 second exemplary system
2800 third exemplary system Although the present invention has been described herein with reference to details of currently preferred embodiments, it is not intended that such details be regarded as limiting the scope of the invention, except as and to the extent that they are included in the following claims—that is, the foregoing description of the present invention is merely illustrative, and it should be understood that variations and modifications can be effected without departing from the scope or spirit of the invention as set forth in the following claims. Moreover, any document(s) mentioned herein are incorporated by reference in their entirety, as are any other documents that are referenced within the document(s) mentioned herein.

We claim:
1. A system to assist in obtaining a blood pressure measurement, said system comprising:
a cuff adapted to be wrapped about a limb of a patient, said cuff including an interior chamber and an exterior surface,
a first adapter connected to the exterior surface of said cuff, said first adapter including an opening continually providing direct fluid communication between said exterior surface and said interior chamber, a second adapter comprising a unitary rigid body, where the unitary rigid body has respective first and second ends, said first end being releasably and directly couplable to said first adapter and in direct fluid communication therewith out intermediate hoses therebetween, said second end of said second adapter having means for allowing individual interchangeable fluid communication of said cuff with any of a plurality of blood pressure measurement devices when said second adapter is coupled to said first adapter, thereby enabling a plurality of blood pressure measurements to be performed using the same cuff; and at least one hose having a first end for releasable connection to the second end of said second adapter and a second end for interchangeable individual connection to any of the plurality of blood pressure measurement devices.

2. The system of claim 1, wherein said first adapter is made from at least two different materials, said at least two different materials of said first adapter having different flexibilities.

3. The system of claim 1, wherein said first adapter is a socket disposed substantially within the exterior surface of said cuff.

4. The system of claim 1, wherein said first adapter has a flange for connection to said cuff.

5. The system of claim 4, wherein said flange is connected to said cuff by a technique selected from the group consisting of welding, bonding, and sealing.

6. The system of claim 5, wherein said flange is connected to said cuff by a welding technique selected from the group consisting of RF welding, ultrasonic welding, chemical welding and heat welding.

7. The system of claim 1, wherein said cuff is formed of a single sleeve having a first edge and a second edge.

8. The system of claim 7, wherein said interior chamber of said cuff is defined by connecting said first edge of said single sleeve to said second edge of said single sleeve.

9. The system of claim 1, wherein the cuff is a reusable cuff.

10. The system of claim 1, wherein the cuff is a disposable cuff.

11. The system of claim 1, wherein said opening has a predetermined diameter and wherein said first adapter includes a radial seal in communication with said cuff.

12. The system of claim 1, wherein said first adapter further comprises an interfacing portion.

13. The system of claim 12, wherein said first adapter is made of a first predetermined material and said interfacing portion is made of a second predetermined material different from said first predetermined material.

14. The system of claim 13, wherein said first predetermined material and said second predetermined material have different flexibilities.

15. The system of claim 14, wherein said first predetermined material is more flexible than the second predetermined material.

16. The system of claim 12, wherein said interfacing portion comprises a ring having a first end extending from said first adapter and a ridge extending from said ring.

17. The system of claim 16, wherein said first adapter is made of a first predetermined material and each of said ring and said ridge are made of a second predetermined material different from said first predetermined material.

18. The system of claim 17, wherein said first predetermined material and said second predetermined material have different flexibilities.

19. The system of claim 18, wherein said first predetermined material is more flexible than said second predetermined material.

20. The system of claim 16, wherein said first adapter is made of a first predetermined material, said ring is made of a second predetermined material, and said ridge is made of a third predetermined material, and wherein said first predetermined material is different than said second predetermined material, said second predetermined material is different than said third predetermined material, and said first predetermined material is different than said third predetermined material.

21. The system of claim 20, wherein said first predetermined material has a different flexibility than each of said second predetermined material and said third predetermined material.

22. The system of claim 21, wherein said first predetermined material is more flexible than each of said second predetermined material and said third predetermined material.

23. The system of claim 1, wherein said cuff has a size selected from the group consisting of an infant size, pediatric size, small adult size, adult size, large adult size, and thigh size.

24. The system of claim 23, wherein said cuff size is denoted by indicia on said cuff.

25. The system of claim 24, wherein said indicia are selected from the group consisting of (a) textual indicia, (b) color indicia, (c) pictorial indicia, and (d) any combination of at least two of (a), (b) and (c).

26. The system of claim 1, wherein said second adapter is releasably connected to said first adapter by a technique selected from the group consisting of: (a) snap fitting, (b) threaded connection, (c) detent action, (d) friction fitting, and (e) a combination of at least two of (a), (b), (c) and (d).

27. The system of claim 1, wherein said second adapter is at least partially rotatable while connected to said first adapter.

28. The system of claim 1, wherein said second adapter is substantially 360° rotatable while connected to said first adapter.

29. The system of claim 1, wherein said second adapter includes at least one screening component for collecting contaminants.

30. The system of claim 29, wherein said at least one screening component is integral to said second adapter.

31. The system of claim 29, wherein said at least one screening component is attached to said second adapter.

32. The system of claim 29, wherein each of the at least one screening component is a substantially cylindrical member.

33. The system of claim 29, wherein each of the at least one screening component is made of a material selected from the group consisting of a mesh material and a membrane.

34. The system of claim 33, wherein the mesh material is selected from the group consisting of a wire screen, a cloth material and a plastic material.

35. The system of claim 33, wherein the membrane is selected from the group consisting of a sintered material, a fibrous material and a fabric.

36. The system of claim 1, wherein each of said at least one hose is selected from the group consisting of (a) a hose having a first end, a second end and a single lumen defined therein, and (b) a hose having a first end, a second end and more than one lumen defined therein.

37. The system of claim 1, wherein said second adapter has at least one barb to enable said second adapter to be individually connected to each of said at least one hose.

38. The system of claim 1, wherein said second adapter has at least one recess to enable said second adapter to be individually connected to each of said at least one hose.

39. The system of claim 1, wherein said second adapter comprises:
   a first chamber in direct fluid communication with said opening;
   a second chamber in direct fluid communication with said opening; and
   a dividing zone between said first chamber and said second chamber, wherein said dividing zone is effective to minimize fluid communication between said first chamber and said second chamber.

40. The system of claim 39, wherein said dividing zone includes a first wall in communication with said first chamber and a second wall in communication with said second chamber, said first wall and said second wall defining a channel therebetween and being separated by a distance of at least 1 mm.

41. The system of claim 39, wherein each of the first chamber and the second chamber includes at least one screening component for collecting contaminants.

42. The system of claim 1, wherein said second adapter comprises a chamber in direct fluid communication with said opening.

43. The system of claim 42, wherein said chamber includes at least one screening component for collecting contaminants.

44. The system of claim 39, wherein the second end of said second adapter is connected to a dual lumen hose having a first lumen and a second lumen, and wherein said first chamber has a first access opening to enable direct fluid communication between said first chamber and said first lumen, and wherein said second chamber has a second access opening to enable direct fluid communication between said second chamber and said second lumen.

* * * * *